United States Patent [19]

Seela et al.

[11] Patent Number: 5,446,139

[45] Date of Patent: Aug. 29, 1995

[54] PURINE ANALOG NUCLEOSIDE AND NUCLEOTIDE COMPOUNDS

[75] Inventors: Frank Seela; Werner Bourgeouis; Rainer Gumbiowski, all of Osnabrück; Angelika Röling, Münster; Helmut Rosemeyer, Osnabrück; Alfred Mertens, Schriesheim; Harald Zilch, Mannheim; Bernhard König, Berg; Edith Koch, Penzberg, all of Germany

[73] Assignee: Boehringer Mannheim GmbH, Mannheim, Germany

[21] Appl. No.: 809,506

[22] PCT Filed: Apr. 23, 1990

[86] PCT No.: PCT/EP90/00650

§ 371 Date: Feb. 21, 1992

§ 102(e) Date: Feb. 21, 1992

[87] PCT Pub. No.: WO91/01325

PCT Pub. Date: Feb. 7, 1991

[30] Foreign Application Priority Data

Jul. 13, 1991 [DE] Germany ............... 39 24 424.5

[51] Int. Cl.[6] ............................................. C07H 19/16
[52] U.S. Cl. ............................ 536/26.7; 536/26.71; 536/26.74; 536/27.11; 536/27.13; 536/27.2; 536/27.21; 536/27.23; 536/27.6; 536/27.61; 536/27.62; 536/27.63; 536/27.7; 536/27.8; 536/27.81
[58] Field of Search ........... 536/26.7, 26.71, 26.74, 536/27.11, 27.13, 27.2, 27.21, 27.23, 27.6, 27.61, 27.62, 27.63, 27.7, 27.8, 27.81; 514/45, 46, 47, 48

[56] References Cited

FOREIGN PATENT DOCUMENTS

| | | | |
|---|---|---|---|
| 0043722 | 7/1981 | European Pat. Off. ............... | 514/47 |
| 0038569 | 10/1981 | European Pat. Off. .......... | 536/27.13 |
| 01795481 | 9/1972 | Germany ............... | 536/27.13 |
| 0696952 | 9/1953 | United Kingdom .............. | 536/27.13 |
| 1176419 | 1/1970 | United Kingdom .............. | 536/27.13 |
| 1474299 | 5/1977 | United Kingdom ............ | 536/27.13 |

OTHER PUBLICATIONS

Journal of Synthetic Organic Chemistry, Verlag et al., pp. 410–411, 04 Apr. 1985.
Nucleosides and Nucleotides, vol. 6, No. 5, Dekker Inc., Sweeney et al., pp. 387–409, 1979.
Journal of Medicinal Chemistry, vol. 25, No. 1, Montgomery et al., pp. 96–98, Jan. 1982.
Sanger et al., Proc. Nat. Acad. Sci., USA, vol. 74, pp. 5463–5467 (1977).

Primary Examiner—Douglas W. Robinson
Assistant Examiner—James O. Wilson
Attorney, Agent, or Firm—Nikaido, Marmelstein, Murray & Oram

[57] ABSTRACT

The invention concerns nucleoside derivatives of the formula I

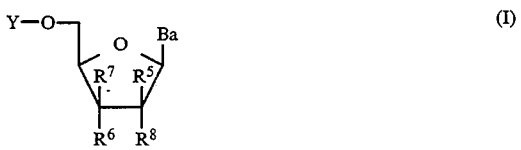

in which Ba signifies an indolyl (A), benzimidazolyl (B), pyrrolopyridinyl (C), imidazopyridinyl (D), triazolopyrimidinyl (E), imidazotriazinyl (F) or imidazopyrimidinyl (G) group substituted by $R^1$, $R^2$ and $R^3$, in which $R^1$, $R^2$ and $R^3$, which can be the same or different, signify hydrogen, halogen, a $C_1$–$C_7$-alkyl, $C_2$–$C_7$-alkenyl, hydroxy, mercapto, $C_1$–$C_7$-alkylthio, $C_1$–$C_7$-alkoxy, $C_2$–$C_7$-alkenyloxy, ar-$C_1$–$C_5$-alkyl, ar-$C_2$–$C_5$-alkenyl, ar-$C_1$–$C_5$-alkoxy, ar-$C_2$–$C_5$-alkenyloxy, aryloxy, nitro, amino-$C_1$–$C_7$-alkyl, $C_1$–$C_7$-alkylamino-$C_1$–$C_7$-alkyl, di-$C_1$–$C_7$-alkylamino-$C_1$–$C_7$-alkyl, amino, a substituted amino group —$NMR^4$ or —$N(R^4)_2$ or an imino group —N=CH—$R^4$, and $R^4$ has the meaning given in the description, $R^5$, $R^6$, $R^7$ and $R^8$ each signify hydrogen or one or two of the radicals $R^5$, $R^6$, $R^7$ and $R^8$ a hydroxyl, halogen, cyano, azido or a substituted amino group —$NHR^4$ or —$N(R^4)_2$ or $R^5$ and $R^7$ can together represent a further bond between C-2' and C-3'

(Abstract continued on next page.)

and Y represents hydrogen or a $C_1$–$C_7$-alkylcarbonyl, monophosphate, diphosphate or triphosphate group, whereby "aryl" signifies a phenyl or naphthyl group and "hetaryl" a furanyl, thienyl or pyridyl group, as well as their possible anomers, $N^7$- or $N^9$-regioisomers (purine nomenclature), tautomers and salts.

12 Claims, No Drawings

PURINE ANALOG NUCLEOSIDE AND NUCLEOTIDE COMPOUNDS

The invention concerns nucleoside and nucleotide derivatives, processes for the preparation of these compounds, as well as their use in the sequencing of nucleic acids.

The subject of the present invention are new nucleoside and nucleotide derivatives of the general formula I

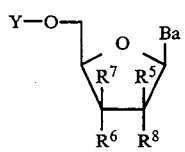
(I)

in which Ba signifies an indolyl (A), benzimidazolyl (B), pyrrolopyridinyl (C), imidazopyridinyl (D), triazolopyrimidinyl (E), imidazotriazinyl (F) or imidazopyrimidinyl (G) radical,

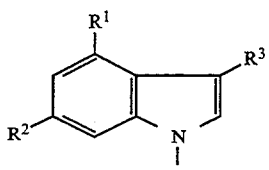
(A)

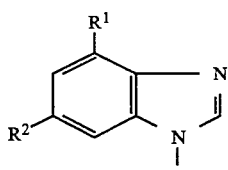
(B)

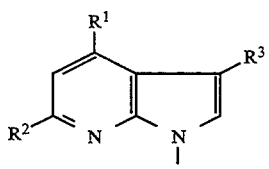
(C)

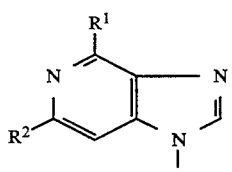
(D)

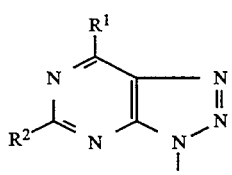
(E)

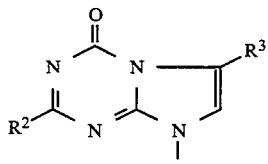
(F)

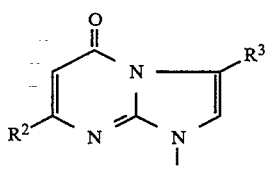
(G)

whereby $R^1$, $R^2$, $R^3$, which can be the same or different, signify hydrogen, halogen, a $C_1$–$C_7$-alkyl, $C_2$–$C_7$-alkenyl, hydroxyl, mercapto, $C_1$–$C_7$-alkylthio, $C_1$–$C_7$-alkoxy, $C_2$–$C_7$-alkenyloxy, ar-$C_1$–$C_5$-alkyl, ar-$C_2$–$C_5$-alkenyl, ar-$C_1$–$C_5$-alkoxy, ar-$C_2$–$C_5$-alkenyloxy, aryloxy, nitro, amino-$C_1$–$C_7$-alkyl, $C_1$–$C_7$-alkylamino-$C_1$–$C_7$-alkyl, di-C-$C_7$-alkylamino-$C_1$–$C_7$-alkyl, amino, a substituted amino group —$NHR^4$ or —$N(R^4)_2$ or an imino group —$N=CH$—$R^4$, whereby $R^4$ can signify a $C_1$–$C_7$-alkyl, $C_2$–$C_7$-alkenyl, $C_3$–$C_7$-cycloalkyl, $C_3$–$C_7$-cycloalkyl-$C_1$–$C_7$-alkyl, $C_3$–$C_7$-cycloalkenyl, $C_1$–$C_7$-alkoxy-$C_1$–$C_7$-alkyl, halogen-$C_1$–$C_7$-alkyl-, hydroxy-$C_1$–$C_7$-alkyl-, ar-$C_1$–$C_5$-alkyl, ar-$C_2$–$C_5$-alkenyl, hetaryl-$C_1$–$C_5$-alkyl or hetaryl-$C_2$–$C_5$-alkenyl group, whereby the aryl and hetaryl moieties can be substituted one, two or three times by $C_1$–$C_6$-alkyl, $C_2$–$C_6$-alkenyl, $C_1$–$C_6$-alkoxy, halogen or hydroxyl, or $R^4$ can signify an amino-$C_1$–$C_7$-alkyl, $C_1$–$C_7$-alkylamino-$C_1$–$C_7$-alkyl or di-$C_1$–$C_7$-alkylamino-$C_1$–$C_7$-alkyl group and, in the case of the —$NHR^4$ and —$N=CH$—$R^4$ group, $R^4$ can additionally be an mino, $C_1$–$C_7$-alkylamino, di-$C_1$–$C_7$-alkylamino or $C_1$–$C_7$-alkoxy group or, in the case of the —$N(R^4)_2$ group, the two nitrogen substituents $R^4$ together form a $C_1$–$C_7$-alkylidene radical which, in turn, can be substituted by a $C_1$–$C_7$-alkoxy, $C_1$–$C_7$-alkylamino or di-$C_1$–$C_7$-alkylamino group, $R^5$, $R^6$, $R^7$ and $R^8$ in each case signify hydrogen or one or two of the residues $R^5$, $R^6$, $R^7$ and $R^8$ signify hydroxyl, halogen, cyano, azido or a substituted amino group —$NHR^4$ or —$N(R^4)_2$ or $R^5$ and $R^7$ can together represent a further bond between C-2' and C-3' and Y represents hydrogen or a $C_1$–$C_7$-alkylcarbonyl, monophosphate, diphosphate or triphosphate group, whereby "aryl" is to signify a phenyl or naphthyl group and "hetaryl" a furanyl, thienyl or pyridyl group, with the proviso that a) for the case that $R^6$ is a hydroxyl group, $R^8$ cannot be a hydrogen atom or a hydroxyl group, b) for the case that Ba is the group (B), cannot be $R^6$ cannot be a halogen or azido group, c) for the case that Ba is the group (D) and $R^2$ hydrogen, $R^1$ cannot be a chlorine or amino group and $R^6$ cannot be a hydrogen or chlorine atom and d) for the case that Ba is the group (E) and $R^1$ the amino group, $R^5$ and $R^7$ cannot together form a bond;

as well as the possible α- and β-anomers thereof, $N^7$-, $N^8$- or $N^9$-regioisomers (purine nomenclature), tautomers and salts, as well as nucleic acids which contain compounds of the formula I as constructional units.

Similar compounds of the formula I are known from EP-A-286,028. The present compounds according to the invention differ structurally from the known compounds by the bases given in the definition of Ba.

The compounds of the general formula I are preponderantly new compounds.

From the prior art are already known a plurality of ribofuranosyl derivatives ($R^6=R^8=OH$), as well as the corresponding 2'-desoxyribofuranosyl derivatives ($R^6=OH$; $R^8=H$) which, however, are not included by the present invention due to the disclaimer a).

Furthermore, from the literature (Bioorg. Khim., 13, 1375, 1987) are known benzimidazoles unsubstituted in the base moiety (base type B) which contain, in the sugar moiety in the 3'-position halogen, azido and amino radicals and which, as triphosphates, have been investigated in vitro with regard to their substrate specificity for DNA biosyntheses. The synthesis of the corresponding nucleosides has also been published (Z. Chem., 25, 180, 1985 and Synthesis, 410/1985). These compounds are not included by the product claim due to the disclaimer b). Of the 3-deazapurinenucleosides (purine nomenclature; base type D), the synthesis is known of derivatives which contain chlorine or an amino group in the 6-position and are substituted in the ribose in the 3'-position by hydrogen or a chlorine atom (Nucleic Acids Res., 15, 1121, 1987 and Nucleosides Nucleotides, 3,413, 1984). These compounds are not included by the product claim due to the disclaimer c). A pharmacological action of these compounds has not been described. In U.S. Pat. No. 3,817,982 is described an 8-aza-6-aminopurine derivative (base type E) with a 2', 3'-didehydro-2', 3'-didesoxyribose radical which can find use as antibiotic, virostatic and in the case of DNA replication studies. This compound is not included by the product and medicament claims due to the disclaimer d).

Furthermore, from the literature are already known some compounds of the formula I in which Y signifies a hydrogen atom (nucleosides) or an alkylcarbonyl group and either $R^6$ and $R^8$ simultaneously represent hydroxyl (ribose derivatives) or $R^6$ hydroxyl and $R^8$ a hydrogen atom (2'-desoxyribose derivatives). These compounds are excluded from the product claim due to the disclaimer a). The same applies to the 2'-desoxyribofuranosylnucleosides with the base type (D) known from EP-A-0,038,569 which possess an inflammation-inhibiting action.

Furthermore, from EP-A-0,043,722 are known β-D-arabinofuranosylnucleosides with the base type (D) as antiviral agents. In the case of these compounds, it is a question of furanosyl derivatives in which $R^5$ and $R^6$ each signify a hydroxyl group and $R^8$ a hydrogen atom. These derivatives are not covered by the claims on the basis of disclaimer a).

For the case that Ba represents the base type (B) or (D), then the $N^7$- and $N^9$-regioisomers are also the subject of the present invention and for the case that Ba represents a triazolopyrimidine group (base type E), also the corresponding $N^7$-, $N^8$- or $N^9$-regioisomers. The separation of the various regioisomers takes place according to per se known methods, such as for example by column chromatography.

The "alkyl" or "alkenyl" moieties in the definition of the substituents $R^1$, $R^2$, $R^3$ and $R^4$ can be straight-chained or branched and contain 1-7, preferably 1-4 carbon atoms. The methyl and the ethyl group are quite especially preferred, for $R^4$ also the propyl and isobutyl group.

By halogen in the definition of the substituents $R^1$, $R^2$, $R^3$, $R^5$, $R^6$, $R^7$ and $R^8$ are understood fluorine chlorine, bromine and iodine, especially preferred is the fluorine and chlorine atom.

The aralkyl, hetaralkyl and aralkoxy radicals occurring in the definitions of the substituents $R^1$, $R^2$, $R^3$ and $R^4$ preferably contain an alkylene chain with 1-5 or 1-3 carbon atoms, respectively, which is substituted once or twice with an aromatic radical, for example phenyl or naphthyl radical. The aryl moieties of the previously mentioned aralkyl, aralkoxy or hetarylalkyl groups can, in turn, be substituted one, two or three times by an alkyl, hydroxyl, halogen or alkoxy group with, in each case, 1-6 preferably 1-3 carbon atoms. The benzyl and hetarylmethyl group is especially preferred as aralkyl group.

As aryloxy radicals in the definition of the substituents $R^1$, $R^2$ and $R^4$, phenyloxy radicals are especially preferred which can possibly be substituted one, two or three times by further substituents, such as for example nitro, alkyl and alkoxy groups, whereby the alkyl and alkoxy groups can contain 1-6 carbon atoms.

By "aryl" are to be understood the phenyl and naphthyl group. The "hetaryl" groups are preferably the furanyl, thienyl or pyridyl group.

The amino group occurring in the definition of the substituents $R^1$, $R^2$, $R^3$, $R^5$, $R^6$, $R^7$ and $R^8$, which can possibly be substituted once or twice by $R^4$, contain, as possible substituents, preferably alkyl, alkenyl, cycloalkyl, alkoxyalkyl, haloalkyl, aralkyl and dialkylaminoalkyl groups, whereby the alkyl and alkenyl moieties of the above-mentioned groups preferably contain 1-5 or 1-3 carbon atoms, respectively.

The two nitrogen substituents $R^4$ can together also represent an alkylidene, preferably a methylidene radical which, in turn, can be substituted by alkoxy or by substituted amino groups. A quite especially preferred substituent of this type is the dimethylaminomethylidene group.

The monophosphate group is the group $-PO(OH)_2$, the diphosphate group the group $-P_2O_3(OH)_3$ and the triphosphate group the group $-P_3O_5(OH)_4$.

As possible salts, there come into question especially alkali metal, alkaline earth metal and ammonium salts of the phosphate groups. As alkali metal salts, lithium, sodium and potassium salts are preferred. As alkaline earth metal salts, magnesium and calcium salts especially come into question. By ammonium salts, according to the invention are understood salts which contain the ammonium ion which can be substituted up to four times by alkyl radicals with 1-4 carbon atoms and/or aralkyl radicals, preferably benzyl radicals. The substituents can hereby be the same or different. The salts of the phosphates can be converted in known manner into the free acids.

The compounds of the formula I can contain basic groups, especially amino groups, which can be converted with suitable acids into acid-addition salts. As acids for this purpose, there come into consideration for example: hydrochloric acid, hydrobromic acid, sulphuric acid, phosphoric acid, fumaric acid, succinic acid, tartaric acid, citric acid, lactic acid, maleic acid or methane-sulphonic acid.

Especially preferred compounds of the general formula I are those which are designated as glyceropentofuranosides, especially their didesoxy, didesoxydidehydro and didesoxy-3'-fluoro derivatives. In this sense, the following meanings of $R^5$–$R^8$ come into question: $R^5$ preferably represents a hydrogen atom or a fluorine atom, $R^7$ a hydrogen atom or a hydroxyl group or $R^5$ and $R^7$ together form a bond. $R^6$ and $R^8$ especially signify a hydrogen atom or a fluorine or azido group.

For $R^1$–$R^3$ and $R^5$–$R^8$, the following groups especially come into question: for $R^1$ hydrogen, amino, chlorine, $C_1$–$C_6$-alkoxy, especially methoxy, or nitro; for $R^2$ hydrogen or amino; for $R^3$ hydrogen; for $R^5$–$R^8$ hydrogen or $R^5$ and $R^7$ together form a bond (2',3'-didesoxy-2',3'-didehydroribofuranosyl derivatives).

Depending upon the base type (A)–(G), for the radicals $R^1$–$R^8$, the following groups especially come into question:

When Ba is the group (A), then $R^1$ preferably signifies an amino or nitro group and $R^2$, $^3$, $R^5$–$R^8$ in each case a hydrogen atom or $R^5$ and $R^7$ together also a bond.

When Ba is the group (B), then $R^1$–$R^3$ and $R^5$–$R^8$ preferably signify a hydrogen atom.

When Ba is the group (C), then $R^1$ preferably signifies a hydrogen atom or an amino or nitro group and $R^2$, $R^3$ and $R^5$–$R^8$ each a hydrogen atom or $R^5$ and $R^7$ together also a bond.

When Ba is the group (D), then $R^1$ preferably signifies an amino or chlorine group and $R^2$, $R^3$, $R^5$–$R^8$ each a hydrogen atom.

When Ba is the group (E), then $R^1$ preferably signifies an amino or a $C_1$–$C_6$-alkoxy group and $R^2$, $R^5$–$R^8$ each a hydrogen atom.

When Ba is the group (F), then $R^2$ preferably signifies a hydrogen atom or an amino group and $R^3$, $R^5$–$R^8$ preferably a hydrogen atom.

When Ba is the group (G), then $R^2$ preferably signifies a hydrogen atom or an amino or chlorine group and $R^3$, $R^5$–$R^8$ a hydrogen atom The compounds according to the invention can be prepared analogously to the known, related compounds. For the preparation of the compounds of the formula I, a process has proved to be especially expedient in which one reacts a compound of the formula II Ba—X     (II)

in which Ba has the above-given meaning and X signifies hydrogen or an alkali metal group, such as e.g. lithium or sodium, with a compound of the formula III

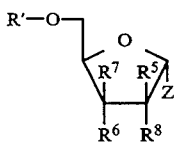

(III)

in which $R^5$, $R^6$, $R^7$ and $R^8$ have the above-given meaning, R' signifies an oxygen protective group and Z a reactive group, to give a compound of the formula IV

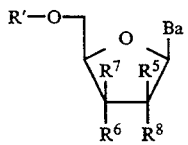

(IV)

in which Ba, $R^1$, $R^2$, $R^3$, $R^5$, $R^6$, $R^7$, $R^8$ and R' have the above-given meaning, and splits off oxygen protective groups possibly present and thereafter possibly converts a compound so obtained, in which $R^5$, $R^6$, $R^7$ or $R^8$ signifies a hydroxyl group, after previous selective protection of the 5'-hydroxyl group, with a halide, cyanide or azide in known manner into a compound of the formula I, in which $R^5$, $R^6$, $R^7$ or $R^8$ signifies halogen or a cyano or azido group, or desoxygenates in known manner to give a compound of the formula I, in which $R^5$, $R^6$, $R^7$ or $R^8$ signifies hydrogen, or reduces a so obtained compound of the formula I, in which $R^5$, $R^6$, $R^7$ or $R^8$ is an azido group, in known manner to give a compound of the formula I, in which $R^5$, $R^6$, $R^7$ or $R^8$ is an amino group, and, if desired, subsequently converts compounds of the formula I, in which Y signifies hydrogen, in known manner into the mono-, di- or triphosphates and, if desired, converts free bases or acids obtained into the corresponding salts or salts obtained into the corresponding free bases or acids.

The compounds of the formula II are reacted with the compounds of the formula III especially advantageously under phase transfer conditions. Under the conditions of phase transfer catalysis, the bases of the formula II are converted into a corresponding anion, for example by means of a 50% aqueous sodium hydroxide solution. The anion thus resulting is hydrophobed by a phase transfer catalyst, for example tris-[2-(2-methoxyethoxy)-ethyl]-amine, and transported into the organic phase in which it reacts with the reactive compound of the formula III.

As reactive group Z in the compounds of the general formula III, there preferably come into question halogen, acetoxy and alkoxy groups. In the case of this reaction, the hydroxyl groups of the sugar residue are protected in the usual way by the oxygen protective groups known to the expert, for example toluoyl, benzoyl, tetrahydropyranyl or acetyl groups. After ending of the reaction, the oxygen protective groups can again be split off in known manner under alkaline conditions, one expediently using a 1M methanolic methanolate solution.

It can be expedient also to keep the radicals $R^1$, $R^2$ and $R^3$ protected during the reaction by means of suitable protective groups. A further advantageous method for the preparation of the compounds of the formula IV is the solid-liquid phase transfer process with the use of solid, powdered potassium hydroxide, the above-mentioned kryptands, as well as the compounds of the formulae II and III in an aprotic solvent.

Compounds of the formula I, in which $R^5$, $R^6$, $R^7$ or $R^8$ signifies halogen or an azido group, are preferably prepared in that one starts from compounds of the formula I, in which $R^5$, $R^6$, $R^7$ or $R^8$ represents a hydroxyl group. The hydroxyl group in the 5'-position is first selectively protected. For this purpose, too, known processes are also available to the expert. For example, in nucleotide chemistry, the 4,4'-dimethoxytriphenylmethyl group has proved to be useful. After the reaction has taken place, this can again be easily split off by mild acid hydrolysis, whereas the also acid-labile glycosidic bond is not hydrolysed under these conditions. The reaction of the nucleoside to be protected with the oxygen protective group reagent for the 5'-hydroxyl group is carried out in a suitable organic solvent, expediently dry pyridine, with a small excess of the oxygen protective group reagent, as well as possibly a suitable adjuvant base, for example N-ethyldiisopropylamine.

The so protected compound of the formula I is reacted with a halide, expediently an alkali metal halide or an organic halide, or with an azide, expediently with an alkali metal azide, such as e.g. lithium azide, in generally known manner. The OH group on the C-2' or C-3' atom is thereby nucleophilically substituted by the halide or azide.

Compounds of the formula I, in which $R^5$, $R^6$, $R^7$ or $R^8$ signifies a hydroxyl group, can also, after previous protection of the 5'-hydroxyl group in the above-given manner, be desoxygenated according to known methods, whereby compounds of the formula I result, in which $R^5$, $R^6$, $R^7$ or $R^8$ signify hydrogen. For this purpose, the compound of the general formula I, in which $R^5$, $R^6$, $R^7$ or $R^8$ represents a hydroxyl group in which the 5'-hydroxyl group has been protected in the above-given manner and also other functional groups carry protective groups, is first converted into a 2'- or 3'-O-thiocarbonyl derivative which is subsequently radical-reduced with tributyl tin hydride. Such methods for the desoxygenation of 2'-desoxynucleosides to 2'- and 3'-didesoxynucleosides are known to the expert. The Barton desoxygenation method has proved to be especially suitable (J. Chem. Soc., Perkin Trans. I (1975) 1574).

Compounds of the formula I, in which $R^5$ and $R^7$ represent a further bond between C-2' and C-3', can be prepared analogously to known related compounds (Robins and Hansske, Tetrahedron Letters, 25, 367, 1984, and literature cited herein). For the preparation of these compounds, a process has proved to be especially expedient in which one reacts the appropriate riboses with acetoxyisobutyryl bromide and subsequently reduces the resulting isomers with a reducing agent, such as e.g. the zinc/copper pair or similar reducing agents, and, after splitting off of the protective group under alkaline conditions, obtains the 2', 3'-didesoxy-2', 3'-didehydro derivative from the crude product obtained.

Besides this process, further processes are described in the literature for the didesoxygenation and simultaneous introduction of the double bond (cf. Jain et al., J. Org. Chem., 39, 30, 1974; Robins et al., J.A.C.S., 98, 8204 and 8213, 1976; Adachi et al., J. Org. Chem., 44, 1404, 1979; Mengel et al., Tetrah. Lett., 4203, 1977; Classon et al., Acta Chem. Scand., B 36,251, 1982; Chu et al., J. Org. Chem., 54, 2217, 1989). Furthermore, these compounds can be prepared from the corresponding 2'-desoxyriboses according to known processes (cf. Horwitz et al., J.A.C.S., 86, 1896, 1964; McCarthy et al., J.A.C.S., 88, 1549, 1966; Samukov et al., Biorg. Khim., 9, 52, 1982) of monodesoxygenation with the simultaneous introduction of the double bond. A further route for the preparation of these compounds is the reaction of a 2', 3'-didesoxy-2', 3'-didehydroribose with an appropriately substituted base derivative Ba, such as is known to an expert from the literature (cf. e.g. EP-A-0,286,028).

Compounds of the formula I, in which $R^5$, $R^6$, $R^7$ or $R^8$ signifies an amino group, are expediently prepared in that one reduces compounds of the formula I in which this residue $R^5$, $R^6$, $R^7$ or $R^8$ represents an azido group. This reduction of the azido group to the amino group can take place according to various generally known methods. The reduction with hydrogen on a palladium-carbon catalyst has proved to be especially advantageous.

The phosphate groups are introduced in known manner into compounds of the general formula I, in which Y signifies hydrogen. One obtains the monophosphates, for example, in that one phosphorylates compounds of the formula I, in which Y signifies hydrogen, with phosphorus oxychloride in trimethyl phosphate. The triethylammonium salts obtained in this way can be converted in known manner into other salts by transsalification. The di- and triphosphates are obtained according to known methods, preferably from the monophosphates, by reaction with o-phosphates or pyrophosphates. Their various salts can also be prepared according to known methods.

The compounds of the formula II are known compounds or can be prepared analogously to known compounds. Such processes of preparation are described, for example in Chem. Bet., 110 (1977), 1462; J. Chem. Soc., 1960, 131 and Tetrahedron Lett., 21 (1980), 3135.

Some of the compounds of the formula III are also known compounds. Compounds which have hitherto not been described can be prepared completely analogously to the known compounds. The preparation of such a compound is described, for example, in Chem. Ber., 93 (1960) 2777 and Synthesis, 1984, 961.

Surprisingly, it has now been found that compounds of the formula I inhibit the multiplication of DNA and RNA viruses at the stage of the virus-specific DNA or RNA transcription. The substances can especially influence the multiplication of retroviruses via the inhibition of the enzyme reverse transcriptase or via a chain breakage of the growing DNA chain (cf. Proc. Natl. Acad. Sci., USA, 83, 1911, 1986 and Nature, 325, 773, 1987 ).

The substances of the formula I according to the invention can also be advantageously used in the DNA sequencing according to Sanger. Especially the sequencing of d(G-C)-rich DNA fragments is made difficult by the formation of secondary structures which lead to a band compression in the region of d(G-C) clusters. By means of the replacement of 2'-desoxyguanosine triphosphate or 2'-desoxyadenosine triphosphate by compounds according to the invention, in which $R^6$ represents a hydroxyl group, the band compression is largely overcome.

The compounds of the formula I according to the invention, in which $R^6$ and $R^7$ signify hydrogen, are used in the DNA sequencing according to Sanger as chain terminators instead of the known 2',3'-didesoxy compounds.

Nucleic acids which, as constructional units, contain one or more compounds of the formula I can be prepared according to known processes (for example, Nucleic Acids Research, 14, No. 5, 1986, p. 2319 et seq.). However, they also result, for example, in the case of the DNA sequencing. If compounds of the formula I, in which $R^6$ signifies a hydroxyl group, are used as constructional units, then a nucleic acid can have several such constructional units; if, as constructional unit, a compound of the formula I is used, in which $R^6$ signifies hydrogen, then such a constructional unit can only be incorporated once, namely at the end of the chain. The nucleic acids according to the invention are made up of 2 to 1000, preferably 8 to 50 nucleotide constructional units. Nucleic acids with 15–30 nucleotide constructional units are especially preferred.

Besides the compounds mentioned in the Examples, in the meaning of the present invention, for example, the following compounds come into question:

1-(2,3-didesoxy-3-fluoro-β-D-glyceropentofuranosyl)-4-amino-1H-indole 1-(2,3-didesoxy-3-azido-β-D-glyceropentofuranosyl)-4-amino-1H-indole
1-(2,3-didesoxy-β-D-glyceropentofuranosyl)-4,6-diamino-1H-indole
1-(2,3-didesoxy-β-D-glyceropentofuranosyl)-6-hydroxy-1H-indole
1-(2,3-didesoxy-β-D-glyceropentofuranosyl)-4-amino-6-hydroxy-1H-indole
1-(2,3-didesoxy-β-D-glyceropentofuranosyl)-4-methylamino-1H-indole
1-(2,3-didesoxy-β-D-glyceropentofuranosyl)-4,6-dihydroxy-1H-indole
1-(2,3-didesoxy-β-D-glyceropentofuranosyl)-4-hydroxy-6-amino-1H-indole
1-(2,3-didesoxy-β-D-glyceropentofuranosyl)-4-methyl-1H-indole
1-(2,3-didesoxy-2,3-didehydro-β-D-glyceropentofuranosyl)-4-amino-6-chloro-1H-indole
1-(2,3-didesoxy-2,3-didehydro-β-D-glyceropentofuranosyl)-4-mercapto-1H-indole
1-(2,3-didesoxy-2,3-didehydro-β-D-glyceropentofuranosyl)-4-methylmercapto-1H-indole
1-(2,3-didesoxy-2,3-didehydro-β-D-glyceropentofuranosyl)-4-methoxy-1H-indole
1-(2,3-didesoxy-2,3-didehydro-β-D-glyceropentofuranosyl)-4-dimethylamino-1H-indole
1-(2,3-didesoxy-2,2-difluoro-β-D-glyceropentofuranosyl)-4-amino-1H-indole
1-(2,3-didesoxy-2-fluoro-β-D-arabinofuranosyl)-4-amino-1H-indole
1-(2,3-didesoxy-2-azido-β-D-arabinofuranosyl)-4-amino-1H-indole
1-(2,3-didesoxy-3-fluoro-β-D-glyceropentofuranosyl)-4-aminobenzimidazole
1-(2,3-didesoxy-3-fluoro-β-D-glyceropentofuranosyl)-4-aminobenzimidazole
1-(2,3-didesoxy-3-azido-β-D-glyceropentofuranosyl)-4-aminobenzimidazole
1-(2,3-didesoxy-β-D-glyceropentofuranosyl)-4,6-diaminobenzimidazole
1-(2,3-didesoxy-β-D-glyceropentofuranosyl)-6-hydroxybenzimidazole
1-(2,3-didesoxy-β-D-glyceropentofuranosyl)-4-amino-6-hydroxybenzimidazole
1-(2,3-didesoxy-β-D-glyceropentofuranosyl)-4-methylaminobenzimidazole
1-(2,3-didesoxy-β-D-glyceropentofuranosyl)-4,6-dihydroxybenzimidazole
1-(2,3-didesoxy-β-D-glyceropentofuranosyl)-4-hydroxy-6-aminobenzimidazole
1-(2,3-didesoxy-β-D-glyceropentofuranosyl)-4-methylbenzimidazole
1-(2,3-didesoxy-2,3-didehydro-β-D-glyceropentofuranosyl)-4-amino-6-chlorobenzimidazole
1-(2,3-didesoxy-2,3-didehydro-β-D-glyceropentofuranosyl)-4-mercaptobenzimidazole
1-(2,3-didesoxy-2,3-didehydro-β-D-glyceropentofuranosyl)-4-methylmercaptobenzimidazole
1-(2,3-didesoxy-2,3-didehydro-β-D-glyceropentofuranosyl)-4-methoxybenzimidazole
1-(2,3-didesoxy-2,3-didehydro-β-D-glyceropentofuranosyl)-4-dimethylaminobenzimidazole
1-(2,3-didesoxy-2,2-difluoro-β-D-glyceropentofuranosyl)-4-aminobenzimidazole
1-(2,3-didesoxy-2-fluoro--D-arabinofuranosyl)-4-aminobenzimidazole
1-(2,3-didesoxy-2-azido-β-D-arabinofuranosyl)-4-aminobenzimidazole 1-(2,3-didesoxy-3-fluoro-β-D-glyceropentofuranosyl)-4-amino-1H-pyrrolo[2,3-b]pyridine
1-(2,3-didesoxy-3-azido-β-D-glyceropentofuranosyl)-4-amino-1H-pyrrolo[2,3-b]pyridine
1-(2,3-didesoxy-β-D-glyceropentofuranosyl)-4,6-diamino-1H-pyrrolo[2,3-b]pyridine
1-(2,3-didesoxy-β-D-glyceropentofuranosyl)-6-hydroxy-1H-pyrrolo[2,3-b]pyridine
1-(2,3-didesoxy-β-D-glyceropentofuranosyl)-4-amino-6-hydroxy-1H-pyrrolo[2,3-b]pyridine
1-(2,3-didesoxy-β-D-glyceropentofuranosyl)-4-methylamino-1H-pyrrolo[2,3-b]pyridine
1-(2,3-didesoxy-β-D-glyceropentofuranosyl)-4,6-dihydroxy-1H-pyrrolo[2,3-b]pyridine
1-(2,3-didesoxy-β-D-glyceropentofuranosyl)-4-hydroxy-6-amino-1H-pyrrolo[2,3-b]pyridine
1-(2,3-didesoxy-β-D-glyceropentofuranosyl)-4-methyl-1H-pyrrolo[2,3-b]pyridine
1-(2,3-didesoxy-2,3-didehydro-β-D-glyceropentofuranosyl)-4-amino-6-chloro-1H-pyrrolo[2,3-b]pyridine
1-(2,3-didesoxy-2,3-didehydro-β-D-glyceropentofuranosyl)-4-mercapto-1H-pyrrolo[2,3-b]pyridine
1-(2,3-didesoxy-2,3-didehydro-β-D-glyceropentofuranosyl)-4-methylmercapto-1H-pyrrolo[2,3-b]pyridine
1-(2,3-didesoxy-2,3-didehydro-β-D-glyceropentofuranosyl)-4-methoxy-1H-pyrrolo[2,3-b]pyridine
1-(2,3-didesoxy-2,3-didehydro-β-D-glyceropentofuranosyl)-4-dimethylamino-1H-pyrrolo[2,3-b]pyridine
1-(2,3-didesoxy-2,2-difluoro-β-D-glyceropentofuranosyl)-4-amino-1H-pyrrolo[2,3-b]pyridine
1-(2,3-didesoxy-2-fluoro-β-D-arabinofuranosyl)-4-amino-1H-pyrrolo[2,3-b]pyridine
1-(2,3-didesoxy-2-azido-β-D-arabinofuranosyl)-4-amino-1H-pyrrolo[2,3-b]pyridine
1-(2,3-didesoxy-β-D-glyceropentofuranosyl)-4-amino-1H-imidazo[4,5-c]pyridine
1-(2,3-didesoxy-3-fluoro-β-D-glyceropentofuranosyl)-4-amino-1H-imidazo[4,5-c]pyridine
1-(2,3-didesoxy-3-azido-β-D-glyceropentofuranosyl)-4-amino-1H-imidazo[4,5-c]pyridine
1-(2,3-didesoxy-β-D-glyceropentofuranosyl)-4,6-diamino-1H-imidazo[4,5-c]pyridine
1-(2,3-didesoxy-β-D-glyceropentofuranosyl)-6-hydroxy-1H-imidazo[4,5-c]pyridine
1-(2,3-didesoxy-β-D-glyceropentofuranosyl)-4-amino-6-hydroxy-1H-imidazo[4,5-c]pyridine
1-(2,3-didesoxy-β-D-glyceropentofuranosyl)-4-methylamino-1H-imidazo[4,5-c]pyridine
1-(2,3-didesoxy-β-D-glyceropentofuranosyl)-4,6-dihydroxy-1H-imidazo[4,6-c]pyridine
1-(2,3 -didesoxy-βD-glyceropentofuranosyl)-4-hydroxy-6-amino-1H-imidazo[4,5-c]pyridine
1-(2,3-didesoxy-β-D-glyceropentofuranosyl)-4-methyl-1H-imidazo[4,5-c]pyridine
1-(2,3-didesoxy-2,3-didehydro-β-D-glyceropentofuranosyl)-4-amino-6-chloro-1H-imidazo[4,5-c]pyridine
1-(2,3-didesoxy-2,3-didehydro-β-D-glyceropentofuranosyl)-4-mercapto-1H-imidazo[4,5-c]pyridine
1-(2,3-didesoxy-2,3-didehydro-β-D-glyceropentofuranosyl)-4-methylmercapto-1H-imidazo[4,5-c]pyridine
1-(2,3-didesoxy-2,3-didehydro-β-D-glyceropentofuranosyl)-4-methoxy-1H-imidazo[4,5-c]pyridine 1-(2,3-didesoxy-2,3-didehydro-β-D-glyceropentofuranosyl)-4-dimethylamino-1H-imidazo[4,5-c]pyridine 1-(2,3-didesoxy-2,2-difluoro-β-D-glyceropentofuranosyl)-4-amino-1H-imidazo[4,5-c]pyridine 1-(2,3-didesoxy-2-fluoro-β-D-arabinofuranosyl)-4-amino-1H-imidazo[4,5-c]pyridine 1-(2,3-didesoxy-2-azido-β-D-arabinofuranosyl)-4-amino-1H-imidazo[4,5-c]pyridine 1-(2,3-didesoxy-β-D-glyceropentofuranosyl)-4-amino-1H-triazolo[4,5-d]pyrimidine 1-(2,3-didesoxy-3-fluoro-β-D-glyceropentofuranosyl)-4-amino-1H-triazolo[4,5-d]pyrimidine 1-(2,3-didesoxy-3-azido-β-D-glyceropentofuranosyl)-4-amino-1H-triazolo[4,5-d]pyrimidine 1-(2,3-didesoxy-β-D-glyceropentofuranosyl)-4,6-diamino-1H-triazolo[4,5-d]pyrimidine 1-(2,3-didesoxy-β-D-glyceropentofuranosyl)-6-hydroxy-1H-triazolo[4,5-d]pyrimidine 1-(2,3-didesoxy-β-D-glyceropentofuranosyl)-4-amino-6-hydroxy-1H-triazolo[4,5-d]pyrimidine 1-(2,3-didesoxy-β-D-glyceropentofuranosyl)-4-methylamino-1H-triazolo[4,5-d]pyrimidine 1-(2,3-didesoxy-β-D-glyceropentofuranosyl)-4,6-dihydroxy-1H-triazolo[4,5-d]pyrimidine 1-(2,3-didesoxy-β-D-glyceropentofuranosyl)-4-hydroxy-6-amino-1H-triazolo[4,5-d]pyrimidine 1-(2,3-didesoxy-β-D-glyceropentofuranosyl)-4-methyl-1H-triazolo[4,5-d]pyrimidine 1-(2,3-didesoxy-2,3-didehydro-β-D-glyceropentofuranosyl)-4-amino-6-chloro-1H-triazolo[4,5-d]pyrimidine 1-(2,3-didesoxy-2,3-didehydro-β-D-glyceropentofuranosyl)-4-mercapto-1H-triazolo[4,5-d]pyrimidine 1-(2,3-didesoxy-2,3-didehydro-β-D-glyceropentofuranosyl)-4-methylmercapto-1H-triazolo[4,5-d]pyrimidine 1-(2,3-didesoxy-2,3-didehydro-β-D-glyceropentofuranosyl)-4-methoxy-1H-triazolo[4,5-d]pyrimidine 1-(2,3-didesoxy-2,3-didehydro-β-D-glyceropentofuranosyl)-4-dimethylamino-1H-triazolo[4,5-d]pyrimidine 1-(2,3-didesoxy-2,2-difluoro-β-D-glyceropentofuranosyl)-4-amino-1H-triazolo[4,5-d]pyrimidine 1-(2,3-didesoxy-2-fluoro-β-D-arabinofuranosyl)-4-amino-1H-triazolo[4,5-d]pyrimidine 1-(2,3-didesoxy-2-azido-β-D-arabinofuranosyl)-4-amino-1H-triazolo[4,5-d]pyrimidine 8-(2,3-didesoxy-β-D-glyceropentofuranosyl)-8H-imidazo[1,2-a]-s-triazin-4-one 8-(2,3-didesoxy-3-fluoro-β-D-glyceropentofuranosyl)-8H-imidazo[1,2-a]-s-triazin-4-one 8-(2,3-didesoxy-3-azido-β-D-glyceropentofuranosyl)-8H-imidazo[1,2-a]-s-triazin-4-one 8-(2,3-didesoxy-β-D-glyceropentofuranosyl)-2-aminoimidazo[1,2-a]-s-triazin-4-one 8-(2,3-didesoxy-β-D-glyceropentofuranosyl)-2-hydroxyimidazo[1,2-a]-s-triazin-4-one 1-(2,3-didesoxy-2,3-didehydro-β-D-glyceropentofuranosyl)-8H-imidazo[1,2-a]-s-triazin-4-one 1-(2,3-didesoxy-2,3-didehydro-β-D-glyceropentofuranosyl)-2-chloro-8H-imidazo[1,2-a]-s-triazin-4-one 1-(2,3-didesoxy-2,2-difluoro-β-D-glyceropentofuranosyl)-8H-imidazo[1,2-a]-s-triazin-4-one 1-(2,3-didesoxy-2-fluoro-β-D-arabinofuranosyl)-8H-imidazo[1,2-a]-s-triazin-4-one 1-(2,3-didesoxy-2-azido-β-D-arabinofuranosyl)-8H-imidazo[1,2-a]-s-triazin-4-one.

The invention is explained in more detail by the following Examples:

EXAMPLE 1

1-(2,3-Didehydro-2,3-didesoxy-β-D-glyceropentofuranosyl)-4-amino-1H-indole.

a) 1-[2-Desoxy-3,5-di-O-(p-toluoyl)-β-D-erythropentofuranosyl]-4-nitro-1H-indole.

To a solution of 4-nitroindole (972 mg, 6.0 mmol) in CH$_3$CN (50 ml) one adds KOH (838 mg, 15.0 mmol) and TDA-1 (100 mg, 0.31 mmol) and stirs for 15 min. at RT (N$_2$ atmosphere). After the addition of the halogenose (2.45 g, 6.3 mmol), one further stirs for 15 min. at RT, filters, evaporates to dryness and chromatographs the residue over a short silica gel-60H column. Evaporation of the main zone and crystallisation from benzene/cyclohexane (1:2) gives yellow needles (2.70 g, 85%) (82%; N. D. Girgis, H. B. Cottam and R. K. Robins, J. Heterocycl. Chem., 25, 361 (1988); Rf (CH$_2$Cl$_2$/EtOAc 99:1)=0.6; Rf (CH$_2$Cl$_2$)=0.4.

$^1$H NMR ([D$_6$]DMSO): δ=2.37, 2.41 (2s, 6H, 2 CH$_3$), 2.78 (m, 1H, H-2'b), 3.03 (m, 1H, H-2'a), 4.56 (m, 3H, H-4' and H-5'), 5.74 (m, 1H, H-3'), 6.75 (dd, J=5.9 Hz and 7.8 Hz, 1H, H-1'), 7.13 (d, J=3.1 Hz, H-3), 7.29–7.40 (m, 5H, aromat. H), 7.83–8.02 (m, 5H, aromat. H and H-6), 8.11 (d, J=7.9 Hz, 1H, H-5), 8.25 (d, J=8.2 Hz, 1H, H-7).

b) 1-(2-Desoxy-β-D-erythro-pentofuranosyl)-4-nitro-1H-indole.

The compound obtained in a) (3.86 g, 7.5 mmol) is mixed with MeOH (200 ml) and, together with NaOMe/MeOH solution (1M, 15.5 ml), stirred for 48 h at room temperature. After the addition of silica gel 60 (50 g), one evaporates to dryness and chromatographs on silica gel 60H (column 3×30 cm, elution agent CHC$_3$/MeOH 8:1, Rf=0.3). Elution of the main zone gives, after evaporation of the solvent, a yellow solid in 80% yield. (96%, N. S. Girgis, H. B. Cottam and R. K. Robins, J. Heterocycl. Chem., 25, 361 (1988)).

$^1$H NMR ([D$_6$]DMSO): δ=2.31 (m, 1H, H-2'b), 2.51 (m, 1H, H-2'a), 3.55 (m, 2H, H-5'), 3.87 (m, 1H, H-4'), 4.40 (m, 1H, H-3'), 4.97 (m, 1H, 5'-OH), 5.36 (m, 1H, 3'-OH), 6.51 (pt, J=6.5 Hz, 1H, H-1'), 7.11 (d, J=3.2 Hz, 1H, H-3), 7.36 (t, J=8.1 Hz, 1H, H-6), 8.03 (d, J=3.2 Hz, 1H, H-2), 8.10 (d, J=8.0 Hz, 1H, H-5), 8.17 (d, J=8.2 Hz, 1H, H-7).

c) 4-Amino-1-(2-desoxy-β-D-erythro-pentofuranosyl)-1H-indole (1,3,7-tridesaza-2'-desoxyadenosine).

1.0 g of the compound obtained in b) is dissolved in 50 ml ethanol and hydrogenated in the presence of 100 mg Pd/carbon (10% Pd) for 6 h at RT and normal pressure. One filters, adsorbs on silica gel and chromatographs on silica gel 60 (column 15×3.5 cm). One obtains a colourless foam (yield 70%) (74%, N. S. Girgis, H. B. Cottam and R. K. Robins, J. Heterocycl. Chem., 25, 361 (1988).

$^1$H NMR ([D$_6$]DMSO): δ=2.17 (m, 1H, H-2'b), 2.42 (m, 1H, H-2'a), 3.51 (m, 2H, H-5'), 3.79 (m, 1H, H-4'), 4.32 (m, 1H, H-3'), 4.89 (m, 1H, 5'-OH), 5.26 (m, NH$_2$ and 3'-OH), 6.23 (m, 2H, H-5 and H-1'), 6.59 (d, J=3.3 Hz, 1H, H-3), 6.71 (d, J=8.2 Hz, 1H, H-7), 6.84 (pt, J=8.2 Hz, 1H, H-6), 7.31 (d, J=3.3 Hz, 1H, H-2).

4-{[(Dimethylamino)-methylene]-amino}-1-(2-desoxy-β-D-erythro-pentofuranosyl)-1H-indole.

1.54 g (6.21 mmol) of the compound obtained in c) are dissolved in 30 ml dry, amine-free dimethylformamide and mixed with 12 ml (68.3 mmol) N,N-dimethylformamide diethylacetal. The reaction mixture is stirred for 8 h at 50° C. under argon. The solvent is evaporated off in a vacuum and the residue subsequently evaporated several times with toluene. Chromatography on silica gel 60 H (column 13×5 cm, elution agent CHCl$_3$/MeOH 5:1) gives 1.28 g (68%) of colourless, foamy product; TLC (CHCl$_3$/MeOH 5:1): Rf=0.4.

$^1$H NMR ([D$_6$]DMSO): δ=2.19 (m, 1H, H-2'b), 2.46 (m, 1H, H-2'a), 3.01 (s, 6H, 2 CH$_3$), 3.51 (m, 2H, H-5'2), 3.81 (m, 1H, H-4'), 4.34 (m, 1H, H-3'), 4.89 (m, 1H, 5'-OH), 5.29 (d, J=4.2 Hz, 1H, 3'-OH), 6.31 (dd, J=6.2 and 7.6 Hz, 1H, H-1'), 7.00 (t, J=7.8 Hz, 1H, H-6), 7.13 (d, J=7.8 Hz, 1H, H-), 7.43 (d, J=3.4 Hz, 1H, H-2), 7.80 (s, 1H, CH).

e) 4-{[(Diemthylamino)-methylene]-amino}-1-[2-desoxy-5-O-(tert.-butyl-diphenylsilyl)-β-D-erythropentofuranosyl]-1H-indole.

1.6 g (5.27 mmol) of the compound obtained in d) are evaporated ×2 with pyridine and subsequently dissolved in pyridine (26 ml). TBDPSiCl (1.63 ml, 6.36 mmol) is added dropwise in the cold and the solution stirred for 30 min at 0° C. One allows to warm to RT and stirs for a further 24 h. The solvent is evaporated off and the residue subsequently evaporated with toluene. UV (MeOH): λ$_{max}$ (ε)=220 (44200), 298 nm (13200).

$^1$H NMR ([D$_6$]DMSO): δ=0.87 (s, 9H, tBu), 2.12 (m, 1H, H-2'b), 2.41 (m, 1H, H-2'a), 2.86 (s, 6H, N(CH$_3$)$_2$), 3.64 (m, 2H, H-5'a,b), 3.78 (m, 1H, H-4'), 4.33 (m, 1H, H-3'), 5.22 (d, J=4.5 Hz, 1H, 3'-OH), 6.20 (pt, J=6.6 Hz, 1H, H-1'), 6.30 (d, J=3.3 Hz, 1H, H-3), 6.36 (d, J=7.4 Hz, 1H, H-), 6.82 (t, J=7.4 Hz, 1H, H-6), 7.01 (d, J=7.4 Hz, 1H, H-), 7.18 (d, J=3.3 Hz, 1H, H-2), 7.20-7.50 (m, 10 phenyl-H), 7.64 (s, 1H, N=CH). C$_{33}$H$_{39}$N$_3$O$_3$Si (553.78) calc. C 71.57%; H 7.10%; N 7.59% found 71.45%; 7.21%; 7.72% f) 4-{[(Dimethylamino)-methylene]-amino}-1-[2-desoxy-5-O-(tert.-butyl-diphenylsilyl)-3O-methyl-sulphonyl-β-D-erythro-pentofuranosyl]-1H-indole.

800 mg (1.44 mmol) of the compound obtained in e) are dissolved in CH$_2$Cl$_2$ (24 ml) and the solution mixed with pyridine (5.5 ml). With ice cooling, methanesulphonyl chloride (2.17 ml, 28.5 mmol) are added dropwise thereto and the mixture stirred at RT (4 h). After the addition of MeOH (6.5 ml), it is diluted with CHCl$_3$ (100 ml) and extracted with 0.1N HCl and H$_2$O (in each case 100 ml). The org. phase is dried over Na$_2$SO$_4$, filtered and the solvent evaporated in a vacuum. After chromatographic working up (silica gel 60H), one obtains 310 mg (34%) of a colourless foam.

$^1$H-NMR ([D$_6$]DMSO): δ=1.02 (s, 9H, t-Bu), 2.62 (m, 1H, H-2'b), 2.87 (m, 1H, H-2'a), 3.00 (s, 6H, 2 CH$_3$), 3.32 (s, 3H, SCH$_3$), 3.82 (m, 2H, H-5'), 4.26 (m, 1H, H-4'), 5.47 (m, 1H, H-3'), 6.40 (dd, J=6.1 and 8.1 Hz, 1H, H-1'), 6.47 (d, J=3.3 Hz, 1H, H-3), 6.51 (d, J=7.5 Hz, 1H,), 6.95 (pt, J=7.5 Hz, 1H, H-6), 7.20 (d, J=7.5 Hz, 1H, H-), 7.40 (m, aromat. H and H-2), 7.64 (m, aromat. H), 7.78 (s, N=CH).

g) 4-[(Dimethylamino)-methylene]-amino-1-(2,3-didesoxy-2,3-didehydro-β-D-glyceropentofuranosyl)-1H-indole.

The compound obtained in f) (420 mg, 0.84 mmol) is dissolved in 50 ml THF and the solution mixed with 10 ml Bu$_4$NF (1M solution in THF). One stirs the solution for 4 h at 50° C., evaporates the solvent in a vacuum and absorbs the residue on silica gel 60. After column chromatography (30×3 cm, CHCl$_3$-MeOH (8:2) Rf=0.5), one obtains a colourless oil.

$^1$H-NMR ([D$_6$]DMSO): δ=3.01 (s, 6H, 2 CH$_3$), 3.46 (m, 2H, H2-5'), 4.77 (m, 1H, H-4'), 4.91 (t, J=5.5 Hz, 1H, 5'-OH), 6.12 (m, 1H, H-2'), 6.49 (m, 3H, H-3' and H-7/H-5 and H-3), 7.00 (m, 2H, H-6 and H-1'), 7.19 (d, J=3.3 Hz, 1H, H-2), 7.23 (d, J=8.4 Hz,1H, H-5/H-7), 7.81 (s, 1H, N=CH).

h) 4-Amino-(2,3-didehydro-2,3-didesoxy-β-D-glyceropentofuranosyl)-1H-indole.

The compound obtained in g) (200 mg) is dissolved in MeOH (5 ml). After the addition of 20 ml conc. NH$_3$ (25%) one boils the solution under reflux. The solvent is evaporated in a vacuum and the residue chromatographed on silica gel (CHCl$_3$/MeOH, 8:2, Rf=0.84; CH$_2$Cl$_2$/MeOH, 95:5, Rf=0.40).

$^1$H-NMR ([D$_6$]DMSO): δ=5.21 (s, NH$_2$), 6.91 (m, H-1'), 7.08 (d, J=3.4 Hz, H-2').

EXAMPLE 2

1-(2,3-Didehydro-2,3-didesoxy-β-D-glyceropentofuranosyl)-4-nitro-1H-indole.

a) 1-[2-Desoxy-5-O-(tert.-butyldiphenylsilyl)-β-D-erythro-pentofuranosyl]-4-nitro-1H-indole.

1.43 (5.14 mmol) of the compound obtained in Example 1b are evaporated ×2 with pyridine, dissolved in 30 ml pyridine, mixed with 1.57 ml (6.11 mmol) TBDPSiCl in the cold, stirred for 30 min at 0° C., stirred for 24 h at RT, Py evaporated off, evaporated ×2 with toluene, adsorbed on silica gel 60 (15 g). Chromatography (column 20×5 cm), Rf (CH$_2$Cl$_2$)=0.2, yellow foam, yield: 1.73 g (65%). UV (MeOH): λ$_{max}$ (ε)=241 (sh. 11900), 338 (4600), 372 (6100).

$^1$H-NMR ([D$_6$]DMSO): δ=0.96 (s, 9H, tBu), 2.30-264 (m, H-2'a,b), 3.79 (m, 2H, H-5'2), 3.97 (m, 1H, H-4'), 4.53 (m, 1H, H-3'), 5.45 (d, J=4.5 Hz, 1H, 3'-OH), 6.55 (pt, J=6.4 Hz, 1H, H-1'), 7.03 (d, J=3.1 Hz, 1H, H-3), 7.28-7.59 (m, 11 aromat. H), 7.90 (d, J=3.1 Hz, 1H, H-2), 8.10 (d, J=8.0 Hz, 1H, H-5), 8.15 (d, J=8.2 Hz, 1H, H-7). C$_{29}$H$_{32}$N$_2$O$_3$Si (516.67) calc. C 67.42%; H 6.24%; N 5.42% found 67.56%; 6.23%; 5.39% b) 1-[2-Desoxy-5-O-(tert.-butyldiphenylsilyl)-3-O-methylsulphonyl-β-D-erythro-pentofuranosyl]-4-nitro-1H-indole.

800 mg (1.55 mmol) of the compound obtained in a) are dissolved in CH$_2$Cl$_2$ (26 ml)/pyridine (6 ml). One mixes, while cooling, with methanesulphonyl chloride (2.36 ml, 31 mmol), allows the mixture to warm slowly to RT and stirs for a further 4 h. One mixes with MeOH (1.7 ml), stirs for a further 15 min., dilutes with CHCl$_3$ (100 ml) and extracts with 0.1N HCl and H$_2$O (in each case 100 ml). The organic phase is dried over Na$_2$SO$_4$. The solvent is evaporated in a vacuum. After chromatography (CH$_2$Cl$_2$, column 30×4 cm, Rf 0.5), one obtains a yellow foam (840 mg, 91%). UV (MeOH): λ$_{max}$ (ε)=235 (sh., 13300), 270 (sh., 1800), 338 (5300), 365 (6300), 388 (sh., 5100).

$^1$H NMR ([D6]DMSO): δ=1.01 (s, 9H, t-Bu), 2.83 (m, 1H, H-2'b), 2.98 (m, 1H, H-2'-a), 3.36 (s, 3H, S-CH$_3$), 3.86 (m, 2H, H-5'), 4.34 (m, 1H, H-4'), 5.53 (m, 1H, H-3'), 6.66 (pt, J=6.2 Hz, 1H, H-1'), 7.08 (d, J=3.3 Hz, 1H, H-3), 7.30-7.62 (aromat. H, as well as H-6), 7.94 (d, J=3.3 Hz, 1H, H-2), 8.14 (d, J=8 Hz, 1H, H-5), 8.23 (d, J=8 Hz, 1H, H-7). C$_{30}$H$_{34}$N$_2$O$_7$SiS (594.76) calc. C 60.58%; H 5.76%; N 4.71%; S 5.39% found 60.45%; 5.76%; 4.74%; 5.54% c) 1-(2,3-Didehydro-2,3-didesoxy-β-D-glyceropentofuranosyl)-4-nitro-1H-indole.

800 mg (1.35 mmol) of the compound obtained in b) are dissolved in 25 ml THF, mixed with 5 ml Bu$_4$NF (1M solution in THF) and the solution stirred for 2 h at 50° C. under N$_2$ atmosphere. The solvent is evaporated off in a vacuum and the residue chromatographed on silica gel (column 30×3.5 cm, elution agent CH$_2$Cl$_2$/MeOH 99:1. Rf 0.3). From the main zone, after evaporating off of the solvent, one obtains a yellow oil which, upon leaving to stand, crystallises through. UV (MeOH): λ$_{max}$ (ε)=237 (11700), 339 (sh., 4700), 370 (6100).

$^1$H NMR ([D$_6$]DMSO): δ=3.51 (m, 2H, H-5'), 4.86 (m, 2H, H-4' and 5'-OH), 6.20 (pq, J=6.0 Hz and 1.7 Hz, 1H, H-2'), 6.54 (pq, J=6.0 Hz and J=1.6 Hz, 1H, H-3'), 7.11 (d, J=3.3 Hz, 1H, H-3), 7.21 (m, 1H, H-1'), 7.40 (t, J=8.1 Hz, 1H, H-6), 7.81 (d, J=3.3 Hz, 1H, H-2), 8.12 (d, J=8.1 Hz, 1H, H-5), 8.27 (d, J=8.1 Hz, 1H, H-7). C$_{13}$H$_{12}$H$_2$O$_4$ (260.25) calc. C 60.00%; H 4.65%; N 10.76% found 60.18%; 4.76%; 10.69%

EXAMPLE 3

4-Amino-1-(2,3-didesoxy-β-D-glyceropentofuranosyl)-1H-indole (1,3,7-tridesaza-2,3-didesoxyadenosine).

150 mg (0.58 mmol) of the compound obtained in Example 2c) are dissolved in 15 ml EtOH and hydrogenated in the presence of 15 mg Pd/C (10% Pd) for 12 h at RT under atmospheric pressure. One filters and evaporates to dryness. The residue is chromatographed on silica gel (Rf (CH$_2$Cl$_2$/MeOH, 97:3)=0.3).

$^1$H NMR ([D$_6$]DMSO): δ=1.91-2.40 (m, 4H, H-2' and H-3'), 3.49 (m, 2H, H-5'), 4.04 (m, 1H, H-4'), 4.81 (t, J=5.5 Hz, 1H, 5'-OH), 5.20 (s, 2H, NH$_2$), 6.15 (dd, J=4.8 Hz and J=6.6 Hz, 1H, H-1'), 6.20 (d, J=7.5 Hz, 1H, H-5), 6.58 (d, J=3.3 Hz, 1H, H-3), 6.71 (d, J=7.5 Hz, 1H, H-7), 6.83 (t, 7.5 Hz, 1H, H-6), 7.32 (d, J=3.3 Hz, 1H, H-2).

EXAMPLE 4

1-(2,3-Didesoxy-β-D-glyceropentofuranosyl)-4-nitro-1H-indole.

a) 5-O-[(1,1-Dimethylethyl)-dimethylsilyl]-2,3-didesoxy-α,β-D-glyceropentofuranosyl) chloride 5-O-[(1,1-dimethylethyl)-dimethylsilyl]-2,3-didesoxy-α,β-D-glyceropentofuranose (1.5 g, 6.5 mmol) [M. Okabe, R. -C. Sun, S. Y. -K. Tam, L. T. Todaro and D. L. Coffen, J. Org. Chem., 53, 4780, 1988) are dissolved in 26 ml tetrahydrofuran and mixed with CCl$_4$ (1 ml) under N$_2$. One cools to −80° C. and mixes dropwise, in the course of 15 min, with tris-(dimethylamino)-phosphine (1.56 ml). After about 2 h, the same amounts of CCl$_4$ and phosphine are again added thereto. After 6 h, the TLC (silica gel, EtOAc/petroleum ether, 2:8) shows an about 50% conversion of the lactol. The cold reaction solution of the halogenose is introduced directly into the previously prepared glycosylation reaction.

b) 1-(2,3-Didesoxy-5-O-(tert.-butyldimethylsilyl)-D-glyceropentofuranosyl)-4-nitro-1H-indole.

1.0 g (6.16 mmol) 4-nitroindole is dissolved in 200 ml MeCN and stirred for 20 min at RT, together with 690 mg (12.32 mmol) KOH and TDA-1. The in situ prepared cold solution of the halogenose obtained in a) (from 12.32 mmol lactol) is injected portionwise into the suspension and the reaction mixture further stirred intensively for 45 min. Insoluble components are filtered off and the filtrate evaporated to dryness. One adsorbs on silica gel 60 (10 g) and chromatographs on silica gel 60H (petroleum ether/EtOAc, 8:2). Evaporation of the main zone provides an anomeric mixture in 60% yield which consists of 30% of the β-anomers and 30% of the α-anomers.

$^1$H NMR ([D$_6$]DMSO: δ=β-anomer: 4.16 (m, 1H, H-4'), 6.42 (dd, J=3.5 Hz and J=6.4 Hz, 1H, H-1'); α-anomer: 4.32 (m, 1H, H-4'), 6.47 (dd, H-1'). C$_{19}$H$_{28}$N$_2$O$_4$Si (376.53) calc. C 60.61%; H 7.50%; N 7.44% found 60.77%; 7.42%; 7.32% c) 1-(2,3-Didesoxy-β-D-glyceropentofuranosyl)-4-nitro-1H-indole.

The β-anomer obtained in b) is dissolved in THF. After the addition of BU$_4$NF (1M solution in THF), one stirs for 30 min at room temperature. The solvent is evaporated in a vacuum and the residue adsorbed on silica gel 60. After column chromatography (CH$_2$Cl$_2$MeOH, 97:3), one obtains the title compound as yellow oil. Rf (CH$_2$Cl$_2$-MeOH, 97:3)=0.4.

$^1$H-NMR ([D$_6$]DMSO): δ=4.11 (m, 1H, H-4'), 4.89 (t, J=5.4 Hz, 1H, 5'-OH), 6.41 (dd, J=4.0 and 6.7 Hz, 1H, H-1'), 7.09 (d, J=3.2 Hz, 1H, H-3), 7.37 (pt, J=8.1 Hz, 1H, H-6), 8.04 (d, J=3.2 Hz, 1H, H-2).

EXAMPLE 4.1

1-(2,3-Didesoxy-β-D-glyceropentofuranosyl)-4-nitro-1H-indole.

The β-anomer obtained in 4b is desilylated analogously to Example 4c. After column chromatography (CH$_2$Cl$_2$-MeOH, 97:3), one obtains the title compound as yellow oil, Rf=0.4.

$^1$H-NMR ([D$_6$]DMSO): δ=4.27 (m, 1H, H-4'), 4.80 (t, J=5.7 Hz, 1H, 5'-OH), 6.49 (dd, J=4.2 Hz and 6.3 Hz, 1H, H-1'), 7.09 (d, J=3.2 Hz, 1H, H-3), 7.38 (pt, J=8.1 Hz, 1H, H-6), 7.93 (d, J=3.2 Hz, 1H, H-2).

EXAMPLE 5

1-(2,3-Didesoxy-β-D-glyceropentofuranosyl)benzimidazole.

a) 1-[2-Desoxy-3,5-di-O-(4-methylbenzoyl)-β-D-erythrofuranosyl]-benzimidazole.

The glycosylation of benzimidazole with 2-desoxy-3,5-di-O-(p-toluoyl)-α-D-erythro-pentofuranosyl chloride took place under the same conditions as described in Example 4b. Data see [Z. Kazimierczuk, R. Stolarski and D. Shugar, Z. Naturforsch., 40c, 715 (1985)].

b) 1-(2-desoxy-β-D-erythro-pentofuranosyl)benzimidazole.

The preparation of this substance takes place from the compound obtained in a) by detoluoylation Lit. as in a).

c) 1-[2-Desoxy-5-O-(tert.-butyldimethylsilyl)-β-D-erythro-pentofuranosyl]-benzimidazole.

1.0 g (4.26 mmol) of the compound obtained in b) is evaporated 2× with pyridine and subsequently dissolved in 20 ml pyridine. In the cold (0° C.), 1.3 ml (1.391 g, 5.06 mmol) TBDPSiCl are added thereto and the solution stirred for 30 min at 0° C. One allows to warm up slowly to room temperature and stirs for a further 24 h.

Chromatography (column 25×4 cm/silica gel 60) gives a colourless oil; treatment with diethyl ether gives colourless crystals of the m.p. 144°-145° C., Rf (CHCl$_3$/MeOH 9:1)=0.45. Yield: 1.24 g (61%). UV (MeOH): λ$_{max}$ (ε)=246 (7500), 252 (sh. 7200), 265 (4800), 273 (4900), 281 (4200).

$^1$H NMR ([D6]DMSO): δ=0.94 (s, 9H, 3 CH$_3$), 2.35 (m, 1H, H-2'b), 2.65 (m, 1H, H-2'a), 3.77 (m, 2H, H-5'), 3.94 (m, 1H, H-4'), 4.49 (m, 1H, H-3'), 5.44 (d, J=4.1 Hz, 1H, 3'-OH), 6.37 (pt, J=6.5 Hz, 1H, H-1'), 7.10–7.66 (m, 14 aromat. H), 8.36 (s, 1H, H-2). C$_{28}$H$_{32}$N$_2$O$_3$Si (472.66) calc. C 71.15%; H 6.82%; N 5.93% found 71.23%; 6.85%; 5.94% d) 1-[2-Desoxy-5-O-(tert.-butyldimethylsilyl)-3-O-phenoxythiocarbonyl-β-D-erythro-pentofuranosyl]-benzimidazole.

500 mg (1.06 mmol) of the compound obtained in c) in anhydrous MeCN (20 ml) are stirred for 16 h at RT with 4-(dimethylaminopyridine (DMAP, 768 mg, 6.36 mmol) and phenoxythiocarbonyl chloride (PTC-Cl, 320 µl, 1, 2.34 mmol). After evaporating off of the solvent, one chromatographs on silica gel 60 H and, from the main zone, obtains a colourless foam (480 mg, 74%). Rf (CH$_2$Cl$_2$/acetone, 95:5)=0.5. UV (MeOH): λ$_{max}$ (ε)=243 (12000), 264 (sh., 5100), 273 (4800), 280 (4100).

$^1$H NMR ([D6]DMSO): δ=1.03 (s, 9H, 3 CH$_3$), 2.88 (m, 1H, H-2'b), 3.06 (m, 1H, H-2'a), 3.99 (m, 2H, H-5'), 4.48 (m, 1H, H-3'), 6.55 (dd, J=5.4 and 9.0 Hz, 1H, H-1'), 7.09–7.84 (m, 19 aromat. H), 8.46 (s, 1H, H-2). C$_{35}$H$_{36}$N$_2$O$_4$SSi (608.84) calc. 69.05%; H 5.96%; N 4.60%; S 5.27% found 69.26%; 5.99%; 4.74%; 5.12% e) 1-[2,3-Didesoxy-5-O-(tert.-butyldimethylsilyl)-β-D-glyceropentofuranosyl]-benzimidazole.

A solution of 350 mg (0.57 mmol) of the compound obtained in d) in anhydrous toluene (20 ml) is stirred in the presence of AIBN (35 mg) and tributyl tin hydride (200 µl) for 3 h at 80° C. under an atmosphere of argon. Chromatographic working. Yield 83%. Rf (CH$_2$Cl$_2$/acetone) 0.4. UV (MeOH): λ$_{max}$ (ε)=247 (7300), 251 (sh., 7100), 265 (4600), 273 (4700), 281 (4100).

$^1$H NMR ([D6]DMSO): δ=0.96 (s, 9H, 3 CH$_3$), 2.13 (m, 2H, H-3'), 2.47 (m, 2H, H-2'), 3.74 (m, 2H, H-5'), 4.26 (m, 1H, H-4'), 6.32 (pt, J=4.8 Hz, 1H, H-1'), 7.22–7.71 (m, 14 aromat. H), 8.42 (s, 1H, H-2). C$_{28}$H$_{32}$N$_2$O$_2$Si (456.66) calc. C 73.65%; H 7.06%; N 6.13% found 73.64%; 7.02%; 6.10% f) 1-(2,3-Didesoxy-β-glycerpentofuranosyl)benzimidazole.

The compound (200 mg) obtained in a) is dissolved in THF mixed with Bu$_4$NF (1M solution in THF) and stirred for 30 min at RT. Evaporation of the solvent and chromatographic working up gives a colourless oil (yield 69%).

$^1$H NMR ([D6]DMSO: δ=2.06 (m, 2H, H-3'), 2.36 (m, 2H, H-2'), 3.55 (m, 2H, H-5'), 4.14 (m, 1H, H-4'), 4.93 (m, 1H, 5'-OH), 6.28 (dd, J=4.1 and 6.5 Hz, 1H, H-1'), 7.27 (m, 2H, H-5 and H-6), 7.68 (m, 2H, H-4 and H-7), 8.51 (s, 1H, H-2).

EXAMPLE 6

1-(2,3-Didesoxy-β-D-glyceropentofuranosyl)benzimidazole.

a) One also obtains the title compound described in Example 5 analogously to Example 2b in that one dissolves 1.0 g (8.48 mmol) benzimidazole in 200 ml MeCN and stirs with KOH (1.9 g) and TDA-1 (0.8 mmol) for 15 min at RT. The in situ prepared cold solution of the halogenose (prepared from 17 mmol lactol) is injected portionwise into the mixture. One further stirs for 30 min at RT, filters and evaporates the solvent in a vacuum. The residue is chromatographed on silica gel 60.

One obtains the α-anomer in 30% yield and the β-anomer in 30% yield.

$^1$H NMR ([D$_6$]DMSO: β-anomer: δ=4.17 (m, 1H, H-4'), 6.26 (dd, 1H, H-1'), 8.42 (s, 1H, H-2); α-anomer: δ=4.34 (m, 1H, H-4'), 6.33 (pt, 1H, H-1'), 8.38 (s, 1H, H-2).

b) After splitting off of the silyl protective group analogously to Example 2c), one obtains the title compound.

EXAMPLE 7

1-(2,3-Didesoxy-β-D-glyceropentofuranosyl)-1H-pyrrolo[2,3-b]pyridine.

a) 1-[2'-Desoxy-5-O-(triphenylmethyl)-β-D-erythropentofuranosyl]-1H-pyrrolo[2,3-b]pyridine.

1.48 g (6.3 mmol) 1-(2-desoxy-β-D-erythropentofuraosyl)-1H-pyrrolo[2,3-b]pyridine [F. Seela and R. Gumbiowski, Heteocycles, 29,795 (1989)] is evaporated twice with, in each case, 30 ml dry pyridine. Subsequently, under argon, one adds thereto 3.55 g (12.6 mmol) triphenylmethyl chloride, as well as 3.3 ml (19 mmol) Hünig base and stirs for 4 h at room temperature.

The reaction mixture is added to 200 ml 5% aqueous NaHCo$_3$ and extracted three times with, in each case, 150 ml CH$_2$Cl$_2$. The combined organic phases are dried with Na$_2$SO$_4$, filtered and chromatographed on silica gel 60 H (column 7×4.5 cm, CH$_2$Cl$_2$/acetone, 8:2). After the evaporation of the main zone, one obtains a colourless foam; 1.75 g (58%). TLC (silica gel, CH$_2$Cl$_2$/acetone, 8:2) Rf 0.8. UV (MeOH): λ$_{max}$ =288 nm (ε=7600).

$^1$H NMR ([D$_6$]DMSO): δ=2.28 (m, 2'-Ha); 2.61 (m, 2'-Hb); 3.17 (d, J=4.8 Hz, 5'-H2); 3.97 (m, 4'-H), 4.39 (m, 4'-H), 5.38 (d, J=4.7 Hz, 3'-OH), 6.53 (d, J=3.6 Hz, 3'-H), 6.76 (pt, J=4.0 Hz, 1'-H), 7.13 (dd, J=7.8 Hz, 5-H), 7.59 (d, J=3.7 Hz, 2-H), 7.97 (dd, J=7.8 Hz, 4-H), 8.24 (dd, J=1.5 Hz, J=4.7 Hz, 6-H). C$_{31}$H$_{28}$N$_2$O$_3$ (476.58) calc. C 78.13%; H 5.92%; N 5.88% found C 78.06%; H 6.04%; N 5.79% b) 1-(2-Desoxy-5-O-triphenylmethyl-3-O-phenoxythiocarbonyl-β-D-erythro-pentofuranosyl)-1H-pyrrolo[2,3-b]pyridine.

A solution of 1.75 g (3.7 mmol) of the compound obtained in a) in 50 ml abs. acetonitrile is mixed under argon with 1.12 g (9.2 mmol) 4-(dimethylamino)pyridine and 1.0 ml (7.4 mmol) phenoxythiocarbonyl chloride and stirred for 48 h at room temperature. After the evaporation of the reaction mixture, the residue is chromatographed on silica gel 60 H (column 10×4 cm, (CH$_2$Cl$_2$). From the main zone are obtained 1.2 g (51%) of a colourless foam. UV (MeOH): λ$_{max}$=285 (ε=8600).

$^1$H-NMR ([D$_6$]DMSO: δ=2.77 (m, 2'-Ha), 3.18 (m, 2'-Hb), 3.38 (m, 5'-H2), 4.42 (m, 4'-H), 5.93 (m, 3'-H), 6.62 (d, J=3.7 Hz, 3-H), 6.81 (dd, J=5.5 Hz, J=9.1 Hz, 1'-H), 7.18 (dd, J=4.7 Hz, J=7.8 Hz, 5-H), 7.67 (d, J=3.7 Hz, 2-H), 8.03 (dd, J=1.4 Hz, J=7.8 Hz, 4-H), 8.24 (dd, J=1.4 Hz, J=4.7 Hz, 6-H) and other arom. protors. C$_{38}$H$_{32}$N$_2$O$_4$S (612.74) calco C 74.49%; H 5.26%; N found C 74.65% H 5.41%; N 4.35% c) 1-(2,3-Didesoxy-5-O-triphenylmethyl-β-D-glyceropentofuranosyl)-1H-pyrrolo[2,3-b]pyridine.

A solution of 1.2 g (1.86 mmol) of the compound obtained in b) in 60 ml absolute toluene is mixed under argon with 90 mg (0.6 mmol) AIBN and 1.1 ml (4 mmol) tributyl tin hydride and stirred for 5 h at 80° C. After the evaporation of the reaction mixture, the residue is chromatographed on silica gel 60 H (column 8×3 cm, $CH_2Cl_2$). From the main zone is obtained 0.8 g (93%) of amorphous product. Recrystallisation from i-PrOH gives colourless needles of the m.p. 115° C. TLC (silica gel, $CH_2Cl_2$/acetone, 95:5), Rf: 0.83. UV (MeOH): $\lambda_{max}$=289 nm ($\epsilon$=8100).

$^1$H-NMR ([D$_6$]DMSO): $\delta$=2.08 (m, 3'-H2), 2.37 (m, 2'-H2), 3.12 (m, 5'-H), 4.24 (m, 4'-H), 6.48 (d, J=3.7 Hz, 3-H), 6.63 (dd, J=4.0 Hz, J=6.9 Hz, 1'-H), 7.13 (dd, J=4.7 Hz, J=7.8 Hz, 5-H), 7.61 (d, J=3.7 Hz, 2-H), 7.97 (dd, J=1.5 Hz, J=7.8 Hz, 4-H), 7.26 (dd, J=1.5 Hz, J=4.7 Hz, 6-H) and other atom. protons. $C_{31}H_{28}N_2O_2$ (460.58) calc. C 80.84%; H 6.13%; N 6.08% found C 80.79%; H 6.16%; N 6.14% d) 1-(2,3-Didesoxy-$\beta$-D-glycerqpentofuranosyl)-1H-pyrrolo[2,3-b]pyridine.

240 mg (0.52 mmol) of the compound obtained in c) are mixed with 30 ml 80% acetic acid and stirred for 3 h at room temperature. The solvent is stripped off under oil pump vacuum and the residue evaporated subsequently several times with water. The residue is chromatographed on silica gel 60 H (column 8×3 cm, $CH_2Cl_2$/ethyl acetate, 95:5). The residue of the main zone is recrystallised from water. 102 mg (90%) of colourless crystals of the m.p. 124°-125° C. UV (MeOH): $\lambda_{max}$=288 nm ($\epsilon$=7500).

$^1$H-NMR ([D$_6$]DMSO): $\delta$=2.08 (m, 3'-H2), 2.31 (m, 2'-H2), 3.56 (m, 5'-H2), 4.08 (m, 4'-H), 4.98 (tr, J=5.5 Hz, 5'-OH), 6.54 (d, J=3.2 Hz, 3-H), 6.59 (pt, J=5.4 Hz, 1'-H), 7.13 (dd, J=4.7 Hz, J=7.7 Hz, 5-H), 7.77 (d, 1H, J=3.2 Hz, 2-H), 7.98 (d, J=7.7 Hz, 4-H), 8.25 (d, J=4.8 Hz, 6-H). $C_{12}H_{14}N_2O_2$ (218.26) calc. C 66.04%; H 6.47%; N 12.83% found C 66.09%; H 6.57%; N 12.84%

EXAMPLE 8

1-(2,3-Dideoxy-$\beta$-D-glyceropent-2-enofuranosyl)-4-nitro-1H-pyrrolo[2,3-b]pyridine.

a) 1-[5-O-((1,1-dimethylethyl)-diphenylsilyl)-(2'-desoxy-$\beta$-D-erythro-pentofuranosyl)]-4-nitro-1H-pyrrolo[2,3-b]pyridine.

1.0 g (3.6 mmol) 1-(2-desoxy-$\beta$-D-erythropentofuranosyl)-4-nitro-1H-pyrrolo[2,3-b]pyridine [F. Seela and R. Gumbiowski, Heterocycles, 29,795 (1989)] is evaporated twice with, in each case, 30 ml dry pyridine, dissolved in 50 ml pyridine and cooled under $N_2$ to 0° C. 1.18 ml (4.6 mmol) 1,1-dimethylethyldiphenylsilyl chloride are now injected in through a septum. Subsequently, one removes the cold bath and leaves to stir for 8 h at room temperature. The reaction mixture is evaporated, the residue is taken up in 200 ml $CHCl_3$, washed twice with, in each case, 40 ml 0.1N HCl and subsequently with a little water and dried over $Na_2SO_4$. The solvent is stripped off and the yellow oil remaining behind is chromatographed on silica gel 60 (column 10×3 cm, $CH_2Cl_2$/acetone, 95:5). From the main zone one obtains, after evaporation, 1.5 g (81%) of a yellow foam. UV (MeOH): $\lambda_{max}$=357, 338 nm ($\epsilon$=4400, 4400).

$^1$H-NMR ([D$_6$]DMSO): $\delta$=0.99 (s, $CH_3$), 2.38 (m, 2'-Hb), 2.63 (m, 2'-Ha), 3.75 (dd, J=4.8 Hz, 10.9 Hz, 5'-H), 3.87 (dd, J=4.8 Hz, 10.9 Hz, 5'-H), 3.96 (m, 4'-H), 4.53 (m, 3'-H), 5.46 (d, J=4.4 Hz, 3'-OH), 6.79 (tr, J=6.6 Hz, 1'-H), 6.98 (d, J=3.6 Hz, 3-H), 7.97 (d, J=5.3 Hz, 5-H), 8.07 (d, J=3.6 Hz, 2-H), 8.53 (d, J=5.3 Hz, 6-H) and other arom. protons. $C_{28}H_{31}N_3O_5Si$ (517.66) calc. C 64.97%; H 6.04%; N 8.12% found C 65.00%; H 6.24%; N 8.01% b) 1-[2-Desoxy-5-O-((1,1-dimethylethyl)-diphenylsilyl)-3-O-methylsulphonyl-($\beta$-D-erythro-pentofuranosyl)]-4-nitro-1H-pyrrolo[2,3-b]pyridine.

To a solution of 1.0 g (1.9 mmol) of the compound obtained in a) in 50 ml $CH_2Cl_2$ one adds 1 ml (13 mmol) methanesulphonic acid chloride and 15 ml pyridine and leaves to stir for 12 h. After ending of the reaction (TLC monitoring), one adds 20 ml methanol thereto and further stirs for 15 min. The reaction mixture is evaporated, the residue mixed with 200 ml $CHCl_3$, washed twice with, in each case, 40 ml 0.1N HCl and subsequently with a little water and dries over $Na_2SO_4$. The solvent is stripped off and the yellow oil remaining behind chromatographed on silica gel 60 (column 8×3cm, $CH_2Cl_2$). From the evaporation residue of the main zone, one obtains a colourless substance which foams in the case of evaporation. 1.04 g (90%). UV (MeOH): $\lambda_{max}$=352, 338 nm($\epsilon$=4400, 4700).

$^1$H-NMR ([D$_6$]DMSO): $\delta$=0.99 (s, $CH_3$, 2.80 (m, 2'-Ha), 3.11 (m, 2'-Hb), 3.90 (m, 5'-H2), 4.32 (m, 4'-H), 5.54 (m, 3'-H), 6.28 (pt, J=6.3 Hz, 1'-H), 7.02 (d, J=4.9 Hz, 3-H), 7.98 (d, J=6.5 Hz, 5-H), 8.09 (d, J=4.9 Hz, 2-H), 8.52 (d, J=5.3 Hz, 6-H) and other arom. protons. $C_{29}H_{33}N_3O_7SSi$ (595.74) calc. C 58.47%; H 5.58%; N 7.03% found C 58.69%; H 5.65%; N 7.03% c) 1-(2,3-Didesoxy-$\beta$-D-glyceropent-2-enofuranosyl)-4-nitro-1H-pyrrolo[2,3-b]pyridine.

To a solution of 400 mg (0.67 mmol) of the compound obtained in b) in 10 ml THF one adds 5 ml 1M tetrabutylammonium fluoride in THF and leaves to stir under reflux for 4 h. The solvent is stripped off in a vacuum and the crude product chromatographed on silica gel 60 (column 10×3 cm, $CH_2Cl_2$/MeOH; 95:5). The evaporation residue is crystallised from isopropanol. 120 mg (68%) of yellow needles of the m.p. 154° C. UV (MeOH): $\lambda_{max}$=358, 338 nm ($\epsilon$=5000, 4700).

$^1$H-NMR ([D$_6$]DMSO): $\delta$=3.57 (m, 5'-H2), 4.87 (m, 4'-H), 4.96 (tr, J=5.4 Hz, 5'-OH), 6.14 (m, 2'-H), 6.52 (m, 3'-H), 7.05 (d, J=3.6 Hz, 3-H), 7.40 (m, 1'-H), 7.99 (d, J=5.3 Hz, 5-H), 8.03 (d, J=3.6 Hz, 2-H), 8.58 (d, J=5.3 Hz, 6-H). $C_{12}H_{11}N_3O_4$ (261.24) calc. C 55.17%; H 4.24%; N 16.09% found C 55.27%; H 4.38%; N 16.03%

Example 9

4-Amino-1-(2,3-didesoxy-$\beta$-D-glyceropentofuranosyl)-1H-pyrrolo[2,3-b]pyridine.

50 mg of the compound obtained in Example 8c) are dissolved in 30 ml methanol and mixed with 0.1 ml pyridine and 10 mg Pd/C (10% Pd). It is hydrogenated for 2 hours at room temperature under normal pressure. The end product is indicated by decolorisation of the solution. The catalyst is filtered off, washed several times with methanol, the filtrate evaporated and the residue chromatographed on silica gel 60 (column 8×1.5 cm, $CH_2Cl_2$/MeOH, 9:1). From the main zone, one obtains 10 mg (22%) of the colourless title compound.

$^1$H-NMR ([D$_6$]DMSO): $\delta$=1.99 (m, 3'-H2), 2.27 (m, 2'-H2), 3.50 (m, 5'-H2), 4.03 (m, 4'-H), 6.16 (d, J=5.4 Hz, 5-H), 6.25 (s, $NH_2$), 6.34 (pt, J=5.98 Hz, 1'-H), 6.52 (d, J=3.6 Hz, 3-H), 7.28 (d, J=3.6 Hz, 2-H), 7.69 (d, J=5.4 Hz, 6-H).

EXAMPLE 10

1-(2,3-Didesoxy-β-D-glyceropentofuranosyl)-1H-pyrrolo[2,3-b]pyridine 5'-triphosphate,triethylammonium salt.

21.8 mg (0.1 mmol) of the compound obtained in Example 7d are dissolved in 250 μl (2.14 mmol) trimethyl phosphate and mixed with 11.7 μl (0.13 mmol) of freshly distilled POCl$_3$ at 4° C. After stirring for 1.5 h at 4° C., a solution of 0.5 mmol bis-(tri-n-butylammonium) pyrophosphate in 1 ml DMF and 100 μl (0.42 mmol) tri-n-butylamine is added thereto. After 1 min, it is neutralised with 1M aqueous triethylammonium bicarbonate solution (TBK) and subsequently the solvent is stripped off in a vacuum. The residue is taken up in 150 ml water and adsorbed on Fraktogel TSK (column: 30×2.6 cm). Gradient elution (360 ml H$_2$O/360 ml 0.5M TBK solution) leads, at 0.49M TBK, to a main zone from which, after evaporation of the solvent, 370 A$_{288}$ units (49%) of colourless, amorphous triphosphate are obtained in the form of the triethylammonium salt. TLC (2-propanol/NH$_3$/H$_2$O: 3:1:1). Rf=0.12; HPLC (LiChrosorb RP-18; 0.1M ammonium acetate/50% acetonitrile: 1 ml/min); Rt=1.95 min; UV (MeOH): λ$_{max}$=288 nm (ε=7500).

$^{31}$P-NMR (D$_2$O; 0.1M tris-HCl (1:1), pH 7.0, 100 mM EDTA): δ=−10.32 (d, J=19 Hz, Pα), −22.04 (t, J=19 Hz, Pβ), −7.46 (d, J=19 Hz, P gamma).

EXAMPLE 11

1-(2,3-Didesoxy-β-D-glyceropent-2-enofuranosyl)-4-nitro-1H-pyrrolo[2,3-b]pyridine 5'-triphosphate, triethylammonium salt.

26 mg (0.1 mmol) of the compound obtained in Example 8c) were phosphorylated as described in Example 10 and worked up. TLC (2-propanol/NH$_3$/H$_2$O, 3:1:1); Rf=0.12. HPLC (LiChrosorb RP-18; 0.1M ammonium acetate 50% acetonitrile; 1 ml/min); Rt=1.91 min; yield 180 A$_{358}$ units (36%) of colourless, amorphous product. UV (MeOH): λ$_{max}$=358 nm(ε=5000).

$^{31}$P-NMR (D$_2$O, 0.1M tris-HCl (1:1), pH 7, 100 mM EDTA): δ=−10.52 (d, J=20 Hz, Pα), −21.75 (t, J=20 Hz, Pβ), −6.18 (d, J=20 Hz, P gamma).

EXAMPLE 12

8-(2,3-Didesoxy-α(β)-D-glyceropentofuranosyl)-8H-imidazo[1,2-a]-s-triazin-4-one.

a) 8-{5-O-[(1,1-Dimethylethyl)-dimethylsilyl]-2,3-didesoxy-α(β)-D-glyceropentofuranosyl}-2-[(2-methylpropionyl)-amino]-8H-imidazo[1,2-a]-s-triazine-4-one.

2-[(2-Methylpropionyl)-amino]-8H-imidazo[1,2-a]-s-triazin-4-one (500 mg, 2.26 mmol) are dissolved in dry MeCN (100 ml) with gentle warming and mixed with K$_2$CO$_3$ (1 g). One adds TDA-1 (50 μl) thereto and leaves the reaction mixture to stir for 10 min at RT. Subsequently, the cold solution of the 5-O-[(1,1-dimethylethyl)-dimethylsilyl]-2,3-didesoxy-D-glyceropentofuranosyl chloride prepared according to Example 4a) is added thereto in eight equal portions at intervals of 2-3 min and the reaction mixture further stirred for 30 min at RT under N$_2$. Thin layer chromatographic reaction monitoring (silica gel, CH$_2$Cl$_2$-MeOH, 9:1) shows a complete reaction to give two products. After filtration through Celite (1 cm), it is evaporated at oil pump vacuum (20°-25° C.) and the residue immediately chromatographed on silica gel 60 H (column: 6×25 cm, CH$_2$Cl$_2$-MeOH, 95:5). From the rapidly moving main zone, one obtains the anomeric mixture which is dissolved in CH$_2$Cl$_2$-MeOH 99:1 and again chromatographed on silica gel 60 H (column: 6×15 cm, CH$_2$Cl$_2$-MeOH 99:1 (1 l), CH$_2$Cl$_2$-MeOH 97:3 (2 1). From the more rapidly moving zone (Rf (silica gel, CH$_2$Cl$_2$-MeOH 9:1) 0.90), one obtains, after evaporation, 250 mg (25%) of the β-anomer as a colourless foam.

$^1$H-NMR ([D$_6$]DMSO): δ=10.33 (s, NH), 7.64 (d, J=2.7 Hz, H-7), 7.58 (d, J=2.7 Hz, H-6), 6.14 (pt, J=3.8 Hz, H-1'), 4.14 (m, H-4'), 3.75 (m, H$_2$-5'), 2.92 (m, CH), 2.40 (m, H$_2$-2'), 2.06 (m, H$_2$-3'), 1.07 and 1.05 (2 s, iBu-Me), 0.84 (s, t-Bu-Me), 0.01 (s, Si-Me).

From the more slowly moving zone (Rf (silica gel, CH$_2$Cl$_2$-MeOH 9:1) 0.85), one obtains, after evaporation, 270 mg (27%) of the β-anomer as a colourless foam.

$^1$H-NMR ([D$_6$]DMSO): δ=10.3 (s, NH), 7.66 (d, J=2.7 Hz, H-7), 7.59 (d, J=2.7 Hz, H-6), 6.19 (dd, J=5.8 Hz, H-1'), 4.51 (m, H-4'), 3.62 (m, H$_2$-5'), 2.94 (m, CH), 2.35 and 1.82 (m, H$_2$-2' and H$_2$-3'), 1.07 and 1.05 (2 s, iBu-Me), 0.88 (s, t-Bu-Me), 0.05 (s, Si-Me).

b) 2-[(2-Methylpropionyl)-amino]-8-(2,3-didesoxy-β-D-glyceropentofuratosyl-8H-imidazo[1,2-a]-s-triazin-4-one.

The β-anomer isolated according to Example 12a is dissolved in dry THF (5 ml) and mixed with Bu$_4$NF (1M in THF, 5 ml). One stirs for 10 min at RT, evaporates to a colourless oil and chromatographs on silica gel 60 H (column: 10×6 cm, 1 l CH$_2$Cl$_2$-MeOH 97:3; 1 l CH$_2$Cl$_2$-MeOH 9:1). From the main zone, one obtains the product (110 mg, 93%) as colourless foam. TLC (silica gel, CH$_2$Cl$_2$-MeOH 9:1): Ref=0.3.

$^1$H-NMR ([D$_6$]DMSO): δ=10.32 (s, NH), 7.77 (d, J=2.7 Hz, H-7), 7.58 (d, J=2.7 Hz, H-6), 6.14 (dd, J=6.4 Hz, 3.7 Hz, H-1'), 4.99 (t, J=5.4 Hz, 5'-OH), 4.11 (m, H-4'), 3.58 (m, H$_2$-5'), 2.93 (m, J=6.8 Hz), 2.38 (m, H$_2$-2'), 2.03 (H$_2$-3'), 1.07 and 1.05 (2 CH$_3$).

c) 2-[(2-Methylpropionyl)-amino]-8-(2,3-dideoxy-α-D-glyceropentofuranosyl-8H-imidazo[1,2-a]-s-triazin-4-one.

The α-anomer isolated according to Example 12a reacted as described in Example 12b and worked up. TLC (silica gel, CH$_2$Cl$_2$-MeOH 9:1) Rf=0.3.

$^1$H-NMR ([D$_6$]DMSO): δ=10.34 (s, NH), 7.67 (d, J=2.6 Hz, H-7), 7.59 (d, J=2.6 Hz, H-6), 6.21 (dd, J=6.5 Hz, 3.8 Hz, H-1'), 4.83 (t, J=5.4 Hz,5'-OH), 4.12 (m, H-4'), 3.43 (m, H$_2$-5'), 2.90 (m, J=6.9 Hz, CH), 2.3 (m, H$_2$-2'), 1.85 and 1.58 (H$_2$-3'), 1.07 and 1.05 (2 CH$_3$).

d) 8-(2,3-Dideoxy-β-D-glyceropentofuranosyl-8H-imidazo[1,2-a]-s-triazin-4-one.

The β-anomer isolated according to Example 12b (75 mg, 0.23 mmol) is dissolved in methanolic ammonia (5 ml) and stirred for 2 h at RT. One evaporates and chromatographs the oily residue on silica gel 60 H (column 6×6 cm; elution agent CH$_2$Cl$_2$-MeOH 9:1). After evaporation of the main zone, one obtains 40 mg (70%) of product as colourless crystals of the m.p. 157°-158° C. (MeOH). TLC (silica gel, CH$_2$Cl$_2$-MeOH 9:1) Rf=0.2.

$^1$H-NMR ([D$_6$]DMSO): δ=7.50 (d, J=2.7 Hz, H-7), 7.34 (d, J=2.7, H-6), 6.03 (dd, J=5.8 Hz, 3.4 Hz, H-1'), 4.99 (t, J=5.8 Hz, 5'-OH), 4.06 (m, H-4'), 3.57 (m, H$_2$-5'), 2.3 (m, H$_2$-2'), 1.97 (m, H$_2$-3').

e) 8-(2,3-Dideoxy-α-D-glyceropentofuranosyl-8H-imidazo[1,2-a]-s-triazin-4-one.

The α-anomer isolated according to Example 12c is reacted and worked up as described in Example 12d. The oily residue is chromatographed on silica gel 60

(column 15×6 cm, elution agent: 1 l CH$_2$Cl$_2$-MeOH 95:5; 2 l CH$_2$Cl$_2$-MeOH 9:1). After evaporation of the main zone, one obtains 60 mg (74%) of product as colourless foam. TLC (silica gel, CH$_2$Cl$_2$-MeOH 9:1): Rf=0.2.

$^1$H-NMR([D$_6$]DMSO): δ=7.39 (d, J=2.7 Hz, H-7), 7.35 (d, J=2.7 Hz, H-6), 6.92 (s, br., NH$_2$), 6.10 (dd, J=3.6 Hz, 6.3 Hz, H-1'), 4.81 (t, J=5.7 Hz, 5'-OH), 4.33 (m, H-4'), 3.40 (m, H$_2$-5'), 2.40 and 2.20 (2 m, H$_2$-2'), 2.20 and 1.83 (2 m, H$_2$-3').

EXAMPLE 13

7-Methoxy-1(2), (3)-(2',3'-didesoxy-α(β)-D-erythropentofuranosyl)-3H-1,2,3-triazolo[4,5d]pyrimidine.

a) To a suspension of powdered KOH (750 mg, 14.3 mmol) in anhydrous MeCN (50 ml) are added at intervals of, in each case, 10 min, TDA-1 (40 µl, 0.12 mmol) and 7-methoxy-3H-1,2,3-triazolo[4,5-d]pyrimidine (900 mg, 6 mmol). After a further 10 min, within the course of 30 min, is added, in 5 ml portions, a cold solution of the t-butyl-dimethylsilyl-2',3'-didesoxy-D-ribofuranosyl chloride (12 mmol), prepared according to Example 4a, in 30 ml THF. The reaction mixture is stirred for a further 30 min, insoluble material filtered off and the filtrate evaporated to dryness at 40° C. under oil pump vacuum. The syrupy residue is immediately flash chromatographed (silica gel 60, column: 30×3 cm, petroleum ether:ethyl acetate, 6:4). One obtains 3 main fractions (I, II, III). Fraction I contains 4 compounds which are separated by multiple chromatography (silica gel 60, column: 25×3 cm, dichloromethane:acetone, 95:5; and column 30×3 cm, petroleum ether:ethyl acetate, 7:3). Fractions II and III each contain one compound. The assignment of the regio- and stereoisomers took place by comparison of the $^{13}$C-NMR data with that of the corresponding desoxy compounds (F. Seela et al., Heterocyclus, 1989, 29, 2193).

b) 7-Methoxy-3-(5'-t-butyldimethylsilyl-2',3'-didesoxy-α-D-erythro-pentofuranosyl)-3H-1,2,3-triazolo[4,5-d]pyrimidine.

The most rapid zone of Fraction I (see 13a) gives 202 mg (9.2%) of product as colourless oil. TLC (silica gel, petroleum ether:ethyl acetate, 7:3) Rf=0.6.

$^1$H-NMR ([D$_6$]DMSO): δ=0.033 and 0.049 (2 s, 2 SiCH$_3$), 0.86 (s, SiC(CH$_3$)$_3$), 1.97 (m, 3'-H), 2.66 (m, 2'-H), 3.66 (m, 5'-H), 4.21 (s, OCH$_3$), 4.40 (m, 4'-H), 6.72 (dd, J=6.8 Hz and 3.3 Hz, 1'-H), 8.76 (s, 5-H).

c) 7-Methoxy-3-(5'-t-butyldimethylsilyl-2',3'-didesoxy-β-D-erythro-pentofuranosyl)-3H-1,2,3-triazolo[4,5-d]pyrimidine.

From the middle zone of Fraction I (see 13a), one obtains 195 mg (8.9%) of product as colourless oil. TLC (silica gel, dichloromethane:acetone, 95:5) Rf=0.65.

$^1$H-NMR ([D$_6$]DMSO): δ=−0.194 and −0.15 (2 s, 2 SiCH$_3$), 0.72 (s, SiC(CH$_3$)$_3$), 2.21 (m, 3'-H), 2.59 and 2.81 (m, 2'-H), 3.55 (dd, J=11.0 Hz and 5.9 Hz, 5'-H), 4.21 (s, OCH$_3$), 4.26 (m, 4'-H), 6.67 (dd, J=7.1 Hz and 1.7 Hz, 1'-H), 8.79 (s, 5-H).

d) 7-Methoxy-2-(5'-t-butyldimethylsiyl-2',3'-didesoxyα-D-erythro-pentofuranosyl)-3H-1,2,3-triazolo[4,5-d]pyrimidine.

The slowest zone of Fraction I (see 13a) (referred to the elution agent dichloromethane:acetone, 95:5) separates after renewed chromatography (elution agent petroleum ether:ethyl acetate, 7:3) into two sub-zones. The more rapid sub-zone gives 172 mg (7.8%) of product as colourless oil. TLC (silica gel, petroleum ether:ethyl acetate, 7:3) Rf=0.5.

$^1$H-NMR ([D$_6$]DMSO: δ=0.058 and 0.065 (2 s, 2 SiCH$_3$), 0.86 (s, SiC(CH$_3$)$_3$), 1.96 (m, 3'-H), 2.5 (m, 2'-H), 3.68 (m, 5'-H), 4.18 (s, OCH$_3$), 4.50 (m, 4'-H), 6.67 (dd, J=5.9 Hz and 2.7 Hz, 1'-H), 8.76 (s, 5-H).

e) 7-Methoxy-2-(5'-t-butyldimethylsilyl-2',3'-didesoxy-β-D-erythro-pentofuranosyl)-3H-1,2,3-triazolo[4,5-d]pyrimidine.

From the slower sub-zone (see 13 d), one obtains 168 mg (7.7%) of product as colourless oil. TLC (silica gel, dichloromethane:acetone, 95:5) Rf=0.55.

$^1$H-NMR ([D$_6$]DMSO): δ=−0.163 and 0.111 (2 s, 2 SiCH$_3$), 0.72 (s, SiC(CH$_3$)$_3$), 2.17 (m, 3'-H), 2.65 and 2.56 (m, 2'-H), 3.66 (m, 5'-H), 4.31 (m, 1'-H), 6.59 (d, J=5.6 Hz, 1'-H), 8.75 (s, 5-H).

f) 7-Methoxy-1-(5''-t-butyldimethylsilyl-2',3'-didesoxy-α-D-erythro-pentofuranosyl)-3H-1,2,3-triazolo[4,5-d]pyrimidine.

Fraction II (see 13a, elution agent petroleum ether:ethyl acetate, 6:4) gives 118 mg (5.4%) of product as colourless oil. TLC (silica gel, petroleum ether:ethyl acetate, 6:4) Rf=0.5.

$^1$H-NMR ([D$_6$]DMSO): δ=0.048 and 0.063 (2 s, 2 SiCH$_3$), 0.87 (s, SiC(CH$_3$)$_3$), 1.98 (m, 3'-H), 2.75 and 2.60 (m, 2'-H), 3.66 (m, 5'-H), 4.20 (s, OCH$_3$), 4.33 (m, 4'-H), 6.77 (dd, J=6.9 Hz and 2.9 Hz, 1'-H), 8.8 (s, 5-H).

g) 7-Methoxy-1-(5'-t-butyldimethylsilyl-2',3'-didesoxy-β-D-erythro-pentofuranosyl)-3H-1,2,3-triazolo[4,5-d]pyrimidine.

Fraction III (see 13a, elution agent petroleum ether:ethyl acetate, 6:4) gives 175 mg (8.0%) of product as colourless oil. TLC (silica gel, petroleum ether:ethyl acetate, 6:4) Rf=0.35.

$^1$H-NMR ([D$_6$]DMSO): δ=−0.24 and −0.20 (2 s,2 SiCH$_3$), 0.67 (s, SiC(CH$_3$)$_3$), 2.15 (m, 3'-H), 2.87 and 2.60 (m, 2'-H), 3.40 (dd, J=11.1 Hz and 3.9 Hz, 5'-H), 4.28 (m, 4'-H), 6.68 (d, J=6.9 Hz, 1'-H), 8.75 (s, 5-H).

h) 7-Methoxy-3-(2',3'-didesoxy-α-D-erythro-pentofuranosyl)-3H-1,2,3-triazolo[4,5-d]pyrimidine.

500 mg (2.0 mmol) of the compound prepared according to 13b are dissolved in 20 ml THF, mixed with 2 ml of a 1.1N solution of Bu$_4$NF in THF and stirred for 2 h at RT. The solvent is evaporated off and the syrupy residue chromatographed on silica gel 60 (column 20×3 cm, dichloromethane:methanol, 9:1). From the main fraction, one obtains 213 mg (62%) of colourless, amorphous product. TLC (silica gel, dichloromethane:methanol 9:1) Rf=0.55.

$^1$H-NMR ([D$_6$]DMSO): δ=1.97 (m, 3'-H), 2.63 (m, 2'-H), 3.47 (m, 5'-H), 4.21 (s, OCH$_3$), 4.36 (m, 4'-H), 4.81 (t, J=5.7 Hz, 5'-OH), 6.74 (dd, J=7.0 Hz and 3.4 Hz, 1'-H), 8.75 (s, 5-H).

i) 7-Methoxy-3-(2', 3'-didesoxy-β-D-erythro-pentofuranosyl)-3H-1,2,3-triazolo[4,5-d]pyrimidine.

The protection removal of the compound prepared in 13c is carried out as described for Example 13h. After 1 h, it is evaporated to dryness and chromatographed on silica gel (column 20×3 cm, dichloromethane:methanol 95:5). From the main fraction, one obtains 291 mg (85%) of product as colourless crystals. TLC (silica gel, dichloromethane:methanol, 9:1) Rf=0.65.

$^1$H-NMR ([D$_6$]DMSO): δ=2.24 (m, 3'-H), 2.63 and 2.74 (m, 2'-H), 3.42 (m, 5'-H), 4.22 (m, 4'-H and OCH$_3$), 4.70 (t, J=5.7 Hz, 5'-OH), 6.66 (dd, J=7.2 Hz and 2.2 Hz, 1'-H), 8.80 (s, 5-H).

7-Methoxy-2-(2',3'-didesoxy-α-D-erythro-pentofuranosyl)-3H-1,2,3-triazolo[4,5-d]pyrimidine.

500 mg (2.0 mmol) of the compound prepared according to 13d are treated as described in Example 13h. After a reaction time of 1.25 h, the solvent evaporated off and the oily residue chromatographed on silica gel 60 (column 20×3 cm, dichloromethane: methanol, 95:5). Evaporation of the main zone gives the product as crystalline compound. TLC (silica gel, dichloromethane:methanol, 9:1) Rf=0.45.

$^1$H-NMR ([D$_6$]DMSO): δ=1.94 and 2.34 (2 m, 3'-H), 2.56 (m, 2'-H), 3.48 (m, 5'-H), 4.18 (s, OCH$_3$), 4.46 (m, 4'-H), 4.85 (t, J=5.8 Hz, 5'-OH), 6.67 (dd, J=6.2 Hz and 2.5 Hz, 1'-H), 8.76 (s, 5-H).

k) 7-Methoxy-2-(2', 3'-didesoxy-β-D-erythro-pentofuranosyl)-3H-1,2,3-triazolo[4,5-d]pyrimidine.

500 mg (2.0 mmol) of the compound prepared according to 13e are treated as described in Example 13h. After a reaction time of 1 h, it is evaporated to dryness and chromatographed on silica gel 60 (column: 20×3 cm, dichloromethane:methanol, 9:1). One thus obtains 286 mg (84%) of amorphous product. TLC (silica gel, dichloromethane:methanol, 9:1) Rf=0.7.

$^1$H-NMR ([D$_6$]DMSO): δ=2.17 (2m, 3'-H), 2.57 (m, 2'-H), 3.50 (m, 5'-H), 4.16 (s, OCH$_3$), 4.28 (m, 4'-H), 4.76 (t, J=5.6 Hz, 5'-OH), 6.60 (dd, J=4.8 Hz and 3.2 Hz, 1'-H), 8.75 (s, 5-H).

7-Methoxy-1-(2',3'-didesoxy-α-D-erythro-pentofuranosyl)-3H-1,2,3-triazolo[4,5-d]pyrimidine.

500 mg (2.0 mmol) of the compound prepared according to 13f are treated as described in Example 3h. After a reaction time of 1 h, it is evaporated to dryness and chromatographed on silica gel 60 (column: 20×3 cm, dichloromethane:methanol, 9;1). From the main fraction, one obtains 246 mg (72%) of product. TLC (silica gel, dichloromethane:methanol, 9:1) Rf=0.6.

$^1$H-NMR ([D$_6$]DMSO): δ=1.97 (m, 3'-H), 2.71 and 2.60 (m, 2'-H9, 3.47 (m, 5'-H), 4.21 (s, OCH$_3$), 4.29 (m, 4'-H), 4.81 (t, J=5.7 Hz, 5'-OH), 6.79 (dd, J=7.4 Hz and 3.3 Hz, 1'-H ) , 8.75 (s, 5-H ).

m) 7-Methoxy-1-'2',3'-didesoxy-β-D-erythro-pentofuranosyl)-3H-1,2,3-triazolo[4,5-d]pyrimidine.

500 mg (2.0 mmol) of the compound prepared according to 13g are treated as described in Example 3h. After a reaction time of 0.5 h, it is evaporated to dryness and chromatographed on silica gel 60 (column: 20×3 cm, dichloromethane:methanol, 9:1). One thus obtains 303 mg (89%) of product. TLC (silica gel, dichloromethane:methanol, 9:1) Rf=0.5.

$^1$H-NMR ([D$_6$]DMSO): δ=2.19 (m, 3'-H), 2.60 and 2.79 (2 m, 2'-H), 3.33 (m, 5'-H), 4.20 (s, OCH$_3$), 4.23 (m, 4'-H), 4.64 (t, J=5.6 Hz, 5'-OH), 6.69 (d, J=5.7 Hz, 1'-H), 8.75 (s, 5-H).

EXAMPLE 14

7-Amino-3-(2',3'-didesoxy-α-D-erythro-pentofuranosyl)-3H-1,2,3-triazolo[4,5-d]pyrimidine.

100 mg (0.4 mmol) of the compound prepared according to 13h are stirred for 24 h at RT in 10 ml of methanolic NH$_3$ (saturated at 0° C). After the solvent has been evaporated off, the crude product is purified by chromatography (silica gel 60, column: 10×2 cm, dichloromethane:methanol, 9:1). From the main fraction, one obtains 69 mg (74%) of product as crystalline solid. TLC (silica gel, dichloromethane:methanol, 9:1) Rf=0.3.

$^1$H-NMR ([D$_6$]DMSO): δ=1.91 and 2.36 (2 m, 3'-H), 2.7–2.5 (2'-H), 3.46 (m, 5'-H), 4.33 (m, 4'-H), 4.80 (t, J=5.7 Hz, 5'-OH), 6.61 (dd, J=7.0 and 3.5 Hz, 1'-H), 8.12 and 8.45 (2s, 2NH), 8.32 (s, 5-H).

EXAMPLE 15

7-Amino-3-(2',3'-didesoxy-β-D-erythro-pentofuranosyl)-3H-1,2,3-triazolo[4,5-d]pyrimidine.

100 mg (0.4 mmol) of the compound prepared according to 13i are treated as described in Example 14. After the solvent has been evaporated off, the crude product is purified by chromatography (silica gel 60, column: 10×2 cm, dichloromethane: methanol, 9:1). After evaporation of the main fraction, one obtains 83 mg (87%) of product which crystallises from methanol in colourless needles of the m.p. 182° C. TLC (silica gel, dichloromethane:methanol, 9:1) Rf=0.54.

$^1$H-NMR ([D$_6$]DMSO): δ=2.24 (m, 3'-H), 2.59 and 2.70 (2 m, 2'-H), 3.46 (m, 5'-H), 4.81 (t, J=5.7 Hz, 5'-OH), 6.55 (dd, J=7.1 and 2.7 Hz, 1-H), 8.47 and 8.14 (2s, 2 NH), 8.33 (s, 5-H).

EXAMPLE 16

7-Amino-2-(2',3'-didesoxy-α-D-erythro-pentofuranosyl)-3H-1,2,3-triazolo[4,5-d]pyrimidine.

100 mg of the compound prepared according to 13j are treated as described in Example 14. The reaction takes 7 h. After evaporation of the solvent and chromatography on silica gel (column 10×2 cm, dichloromethane:methanol, 9:1), one obtains crystalline product. TLC (silica gel, dichloromethane:methanol, 9:1) Rf=0.5.

$^1$H-NMR ([D$_6$]DMSO): δ=1.94 and 2.35 (2 m, 3'-H), 2.55 (m, 2'-H), 3.49 (m, 5'-H), 4.43 (m, 4'-H), 4.85 (t, J=5.3 Hz, 5'-OH), 6.56 (pt, J=4.5 Hz, 1'-H), 8.1 (s, NH$_2$), 8.32 (s, 5-H).

EXAMPLE 17

7-Amino-2-(2',3'-didesoxy-β-D-erythro-pentofuranosyl)-3H-1,2,3-triazolo[4,5-d]pyrimidine.

100 mg of the compound prepared according to 13k are treated as described in Example 14. After 8 h, it is evaporated to dryness and chromatographed on silica gel (column 10×2 cm, dichloromethane:methanol, 9:1). TLC (silica gel, dichloromethane:methanol, 9:1) Rf=0.35.

$^1$H-NMR ([D$_6$]DMSO): δ=2.17 (m, 3'-H), 2.54 (m, 2'-H), 3.48 (pt, J=5.6 Hz, 5'-H), 4.24 (m, 4'-H), 4.75 (t, J=5.6 Hz, 5'-OH), 6.47 (d, J=4.4 Hz, 1'-H), 8.10 (s, NH), 8.32 (s, NH and 5-H).

EXAMPLE 18

7-Amino-1-(2',3'-didesoxy-α-D-erythro-pentofuranosyl)-3H-1,2,3-triazolo[4,5-d]pyrimidine.

100 mg of the compound prepared according to 13l are treated as described in Example 14. After 36 h, the solvent is evaporated off and the crude product purified by chromatography (silica gel 60, column: 10×2 cm, dichloromethane:methanol, 9:1). After evaporation of the main fraction, one obtains 63 mg (67%) of product which crystallises from acetone in fine needles. TLC (silica gel, dichloromethane :methanol, 9:1) Rf=0.25.

$^1$H-NMR ([D$_6$]DMSO): δ=1.93 and 2.15 (2 m, 3'-H), 3.51 (m, 5'-H), 4.17 (m, 4'-H), 4.91 (t, J=5.7 Hz, 5'-OH), 6.76 (dd, J=6.3 Hz and 1.7 Hz, 1'-H), 7.78 (s, NH$_2$), 8.35 (s, 5-H).

EXAMPLE 19

7-Amino-1-(2′,3′-didesoxy-β-D-erythro-pentofuranosyl)-3H-1,2,3-triazolo[4,5-d]pyrimidine.

100 mg of the compound prepared according to 13m are treated as described in Example 14. After 36 h, it is evaporated to dryness and chromatographed on silica gel (column: 10×2 cm, dichloromethane:methanol, 9:1). From the main zone, there are obtained 58 mg (62%) of crystalline product. TLC (silica gel, dichloromethane:methanol, 9:1) Rf=0.25.

1H-NMR ([$D_6$]DMSO): δ=1.93 and 2.16 (2 m, 3′-H), 2.49 (m, 2′-H), 3.15 (m, 5′-H), 4.36 (m, 4′-H), 4.77 (t, J=5.2 Hz, 5′-OH), 6.64 (dd, J=4.5 Hz, 1′-H), 7.76 (s, $NH_2$), 8.33 (s, 5-H).

EXAMPLE 20

4-Amino-1-(2,3-didesoxy-α(β)-D-glyceropentofuranosyl)-1H-imidazo[4,5-c]pyridine.

a) 4-Chloro-1-(5-O-[(1,1-dimethylethyl)-dimethylsilyl]-2,3-dideoxy-α(β)-D-glyceropentofuranosyl)-1H-4,5-c]pyridine.

4 Chloroimidazo[4,5-c]pyridine (809 mg, 5.3 mmol) is reacted as described in Example 12a with 5-O-[(1,1-dimethylethyl)-dimethylsilyl]-2,3-dideoxy-D-glyceropentofuranosyl chloride (prepared from 2.6 g, 11 mmol of the lactol) and worked up. [TLC (silica gel, $CH_2Cl_2$-MeOH 95:5): Rf=0.77]. The anomeric mixture, obtained as colourless oil, is dissolved in EtOAc-petroleum ether 3:7 and chromatographed on silica gel 60 H (column: 35×6 cm, 0.8 bar, EtOAc-petroleum ether, 3:7). From the more quickly moving zone, one obtains, after evaporation, 390 mg (23%) of the α-anomer as colourless crystals of the m.p. 65°–68° C. (EtOAc).

1H-NMR ([$D_6$]DMSO): δ=8.63 (s, H-1), 8.18 (d, J=5.6 Hz, H-6), 7.73 (d, J=5.6 Hz, H-7), 6.39 (dd, J=6.4, 4.0 Hz, H-1′), 4.39 (m, H-4′), 3.65 (m, $H_2$-5′), 2.4 (m, $H_2$-2′), 2.20 (m, $H_α$-3′), 1.94 (m, $H_β$-3′), 0.87 (s, t-Bu-Me), 0.06 (s, Si-Me).

From the more slowly moving zone, after evaporation, one obtains 420 mg (25%) of the β-anomer as colourless foam.

1N-NMR ([$D_6$]DMSO): δ=8.65 (s, H-2), 8.14 (d, J=5.6 Hz, H-6), 7.75 (d, J=5.6 Hz, H-7), 6.31 (pt, J=4.3 Hz, H-1′), 4.20 (m, H-4′), 3.69 (m, $H_2$-5′), 2.5 (m, $H_2$-2′), 2.04 (m, $H_2$-3′), 0.78 (s, t-Bu-Me), 0.05–0.07 (s, Si-Me).

b) 4-Chloro-1-(2,3-didesoxy-β-D-glyceropentofuranosyl)-1H-imidazo[4,5-c]pyridine.

The β-anomer obtained in Example 20a (300 mg, 0.9 mmol) is dissolved in THF (5 ml) and mixed with $Bu_4NF$ (1M in THF, 5 ml) and stirred for 15 min at RT. One evaporates to a colourless oil and chromatographs on silica gel 60H (column 10×6 cm, 0.5 bar, $CH_2Cl_2$-MeOH 9:1). After evaporation of the main zone, one obtains 170 mg (86%) of product as colourless oil. TLC (silica gel, $CH_2Cl_2$-MeOH 9:1) RF=0.45.

1H-NMR ([$D_6$]DMSO): δ=8.73 (s, H-2), 8.15 (d, J=5.6 Hz, H-6), 7.78 (d, J=5.6 Hz, H-7), 6.32 (dd, J=6.4 Hz, 3.4 Hz, H-1′), 4.98 (t, J=5.3 Hz, 5′-OH), 4.13 (m, H-4′), 3.53 (m, $H_2$-5′), 2.4 (m, $H_2$-2′), 2.05 (m, $H_2$-3′).

c) 4-Chloro-1-(2,3-dideoxy-α-D-glyceropentofuranosyl)-1H-imidazo[4,5-c]pyridine.

The α-anomer obtained in Example 20a (300 mg, 0.9 mmol) is reacted as described in Example 12b and worked up. One obtains 160 mg (81%) of colourless crystals. TLC (silica gel, $CH_2Cl_2$-MeOH 9:1) Rf=0.42.

1H-NMR ([$D_6$]DMSO): δ=8.64 (s, H-2), 8.17 (d, J=5.6 Hz, H-6), 7.74 (d, J=5.6 Hz, H-7), 6.39 (dd, J=6.2 Hz, 4.1Hz, H-1′), 4.86 (t, J=5.3 Hz, 5′-OH), 4.34 (m, H-4′), 3.46 (m, $H_2$-5′), 2.5 (m, $H_2$-2′), 2.19 and 1.93 (2m, $H_2$-3′).

d) 4-Amino-1-(2,3-dideoxy-β-D-glyceropentofuranosyl)-1H-imidazo[4,5-c]pyridine.

The product obtained in Example 20b (100 mg, 0.46 mmol) is mixed with hydrazine hydrate (100%, 10 ml) and stirred for 90 min at 90°–100° C. under $N_2$. After evaporation of excess hydrazine hydrate, it is repeatedly evaporated with EtOH and the residue dissolved in EtOH (25 ml). One adds 2 g of Raney nickel thereto and boils under reflux for 2 h. After filtering off of the catalyst, the filtrate is evaporated and the residue chromatographed on silica gel 60H (column: 6×6 cm, 0.5 bar, $CH_2Cl_2$-MeOH 9:1). After evaporation of the main zone, one obtains 40 mg (37%) of the title compound as colourless foam. TLC (silica gel, $CH_2Cl_2$-MeOH 9:1) Rf=0.4.

1H-NMR ([$D_6$]DMSO): δ=8.33 (s, H-2), 7.67 (d, J=5.8 Hz, H-6), 6.65 (d, J=5.8 Hz, H-7), 6.25 (s, br., $NH_2$), 6.14 (dd, J=6.5 Hz, 3.8 Hz, H-1′), 4.12 (m, H-4′), 3.53 (m, $H_2$-5′), 2.33 (m, $H_2$-2′), 2.01 (m, $H_2$-3′).

EXAMPLE 21

1-(2,3-Didesoxy-β-D-glyceropentofuranosyl)-imidazo[1,2-a]pyrimidin-2-one.

a) 7-Chloro-1-(2,3-didesoxy-5-O-(tert.-butyldimethsilyl)-β-D-glyceropentofuranosyl)-imidazo[1,2-a]-pyrimidin-5-one and its α-anomer 1.0 g (5.9 mmol) 7-chloroimidazo[1,2-a]-pyrimidin-5-one (R. G. Revankar et al., Anm. N.Y. Acad. Sci., 255, 166, 1975) is dissolved in a mixture of 10 ml DMF and 50 ml THF and stirred with 3.0 g KOH and 30 μl TDA-1 for 30 min at room temperature. 5-O-[(1,1-Dimethylethyl)dimethylsilyl] -2,3-didesoxy-D-glyceropentofuranosyl chloride (13 mmol) prepared in situ according to Example 4a, are injected therein in 4 portions. One further stirs for 45 min at room temperature, filters, adds 300 ml of saturated $NaHCO_3$ solution thereto and extracts the aqueous phase with $CHCl_3$. The organic extract is dried with $Na_2SO_4$ and evaporated in a vacuum. Chromatography on silica gel 60 gives 450 mg (20%) of the α-anomer (rapid zone) as colourless oil and 590 mg (26%) of the β-anomer (slow zone) as colourless crystals of the m.p. 63° C. (ether).

(β-anomer): 1H-NMR ([$D_6$]DMSO): δ=0.06 (s, 6H, $CH_3$), 0.87 (s, 9H, $CH_3$), 1.68 (m, 2H, H-3′), 2.25 (m, 2H, H-2′), 3.62 (m, 2H, H-5′), 4.45 (m, 1H, H-4′), 5.99 (s, 1H, H-6), 6.27 (dd, J=3.9 Hz, J=6.8 Hz, 1H, H-1′), 7.73 (d, J=2.7 Hz, 1H, H-3), 7.80 (d, J=2.7 Hz, 1H, H-2). (α-anomer): δ=0.02 (s, 6H, $CH_3$), 0.64 (s, 9H $CH_3$), 2.02 (m, 2H, H-3′), 2.38 (m, 2H, H-2′), 3.76 (m, 2H, H-5′), 4.14 (m, 1H, H-4′), 5.99 (s, 1H, H-6), 6.21 (m, 1H, H-1′), 7.72 (d, J=2.4 Hz, 1H, H-3), 7.79 (d, J=2.4 Hz, 1H, H-2).

b) 7-Chloro-1-(2,3-didesoxy-β-D-glyceropentofuranosyl)-imidazo[1,2-a]pyrimidin-5-one 250 mg (0.65 mmol) of the β-anomer prepared according to a) are dissolved in THF, mixed with 2 ml $Bu_4NF$ (1M solution in THF) and stirred for 60 min at room temperature. After the evaporation off of the solvent, one chromatographs on a 20×2 cm silica gel 60 column. The main zone gives the product as colourless crystals (74%) of the m.p. 157° C. (propanol-2).

$^1$H-NMR ([D$_6$]DMSO): δ=2.00 (m, 2H, H-3'), 2.37 (m, 2H, H-2'), 3.60 (m, 2H,H-5'), 4.10 (m, 1H, H-4'), 5.01 (t, J=5.4 Hz, 1H, OH), 5.99 (s, 1H, H-6), 6.22 (dd, J=217 Hz, J=6.7 Hz, 1H, H-1'), 7.73 (d, J=2.6 Hz, 1H, H-3), 7.92 (d, J=2.6 Hz, 1H, H-2).

c) 1-(2,3-Didesoxy-β-D-glycerqpentofuranosyl-)imidazo[1,2-a]pyrimidin-5-one 60 mg (0.22 mmol) of the compound prepared according to b) are dissolved in 50 ml ethanol. One adds 4 ml conc. NH$_3$ thereto and hydrogenates with 100 mg of Pd (10% Pd on C) for 14 h at RT. The catalyst is filtered off, washed with hot ethanol and the filtrate evaporated. Flash chromatography on silica gel 60 gives 12 mg (23%) of product.

$^1$H-NMR ([D$_6$]DMSO): δ=2.00 (m, 2H, H-3'), 2.30 (m, 2H, H-2'), 3.60 (m, 2H, H-5'), 4.10 (m, 1H, H-4'), 5.03 (t, J=5.4 Hz, 1H, OH), 5.90 (d, J=6.3 Hz, 1H, H-6), 6.28 (dd, J=3.2 Hz, J=6.8 Hz, 1H, H-1'), 7.68 (d, J=2.7 Hz, 1H, H-3), 7.86 (d, J=2.7 Hz, 1H, H-2), 7.94 (d, J=6.3 Hz, 1H, H-7).

EXAMPLE 22

7-Amino-1-(2,3-didesoxy-β-D-glyceropentofuranosyl-)imidazo[1,2-a]pyrimidin-5-one.

One obtains the title compound from 60 mg (0.22 mmol) of the compound prepared according to Example 21b) analogously to the procedure for the corresponding ribo compound (R. G. Revanker et al., Anm. New York Sci., 255, 166, 1975). TLC (silica gel, dichloromethane:methanol, 9:1) Rf=0.35.

We claim:

1. Nucleoside derivatives of formula I

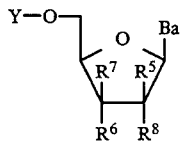
(I)

wherein Ba is an indolyl (A), benzimidazolyl (B), pyrrolopyridinyl (C), imidazopyridinyl (D), triazolopyrimidinyl (E), imidazotriazinyl (F) or imidazopyrimidinyl (G) group, of the following formulae, respectively:

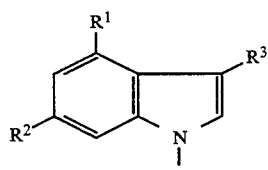
(A)

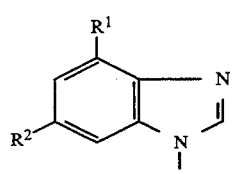
(B)

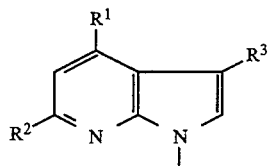
(C)

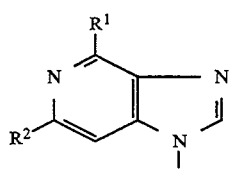
(D)

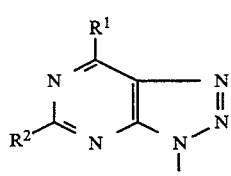
(E)

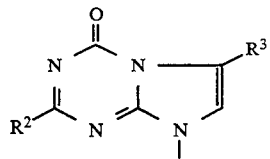
(F)

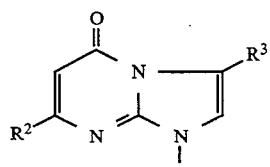
(G)

wherein R$^1$, R$^2$, R$^3$, which can be the same or different, are hydrogen, halogen, C$_1$-C$_7$-alkyl, C$_2$-C$_7$-alkenyl, hydroxy, mercapto, C$_1$-C$_7$-alkylthio, C$_1$-C$_7$-alkoxy, C$_2$-C$_7$-alkenyloxy, aryl-C$_1$-C$_5$-alkyl, aryl-C$_2$-C$_5$-alkenyl, aryl-C$_1$-C$_5$-alkoxy, aryl-C$_2$-C$_5$-alkenyloxy, aryloxy, nitro, amino-C$_1$-C$_7$-alkyl, C$_1$-C$_7$-alkylamino-C$_1$-C$_7$-alkyl, di-C$_1$-C$_7$-alkylamino-C$_1$-C$_7$-alkyl, amino, substituted amino group of the formula —NHR$^4$ or —N(R$^4$)$_2$ or an imino group —N=CH—R$^4$, wherein R$^4$ is C$_1$-C$_7$-alkyl, C$_2$-C$_7$-alkenyl, C$_3$-C$_7$-cycloalkyl, C$_3$-C$_7$-cycloalkyl-C$_1$-C$_7$-alkyl, C$_3$-C$_7$-cycloalkenyl, C$_1$-C$_7$-alkoxy-C$_1$-C$_7$-alkyl, halogen-C$_1$-C$_7$-alkyl, hydroxy-C$_1$-C$_7$-alkyl, aryl-C$_1$-C$_5$-alkyl, aryl-C$_2$-C$_5$-alkenyl, hetaryl-C$_1$-C$_5$-alkyl or hetaryl-C$_2$-C$_5$-alkenyl radical, wherein the aryl and hetaryl moieties are unsubstituted or are substituted one, two or three times by C$_1$-C$_6$-alkyl, C$_2$-C$_6$-alkenyl, C$_1$-C$_6$-alkoxy, halogen or hydroxyl, or R$^4$ is amino-C$_1$-C$_7$-alkyl, C$_1$-C$_7$-alkylamino-C$_1$-C$_7$-alkyl or di-C$_1$-C$_7$-alkylamino-C$_1$-C$_7$-alkyl and, in the case of the —NHR$^4$ and —N=CH—R$^4$ groups, R$^4$ can additionally be amino, C$_1$-C$_7$-alkylamino, di-C$_1$-C$_7$-alkylamino or C$_1$-C$_7$-alkoxy or, in the case of the —N(R$^4$)$_2$ group, the two nitrogen substituents R$^4$ together can form a C$_1$-C$_7$-alkylidene group which, in turn, can be unsubstituted or substituted by C$_1$-C$_7$-alkoxy, C$_1$-C$_7$-alkylamino or di-C$_1$-C$_7$-alkylamino, wherein said aryl is phenyl or naphthyl and said hetaryl is furanyl, thienyl or pyridyl, R$^5$, R$^6$, R$^7$, and $R^8$ each are hydrogen, or one or two of $R^5$, $R^6$, $R^7$, and $R^8$ are hydroxyl, halogen, cyano, azido or a substituted amino group —$NHR^4$ or —$N(R^4)_2$, or and $R^5$ and $R^7$ can together represent a further bond between C-2' and C-3', and Y is hydrogen or $C_1$–$C_7$-alkylcarbonyl, monophosphate, diphosphate or triphosphate, with the provisos that a) when $R^6$ is a hydroxyl group, $R^8$ is other than a hydrogen atom or a hydroxyl group, b) when Ba is the group (B), $R^6$ is other than a halogen, amino or azido group, c) when Ba is the group (D) and $R^2$ is hydrogen, $R^1$ is other than chlorine or amino and $R^6$ is other than hydrogen or chlorine, and d) When Ba is the group (E) and $R^1$ is amino, $R^5$ and $R^7$ cannot together represent a bond, as well as their possible $\alpha$ and $\beta$-anomers, , $N^7$-, $N^8$- or $N^9$ regioisomers (purine nomenclature), tautomers and salts, and nucleic acids which contain compounds of the formula I as constructional units.

2. Nucleoside of claim 1, wherein $R^1$ is hydrogen, amino, $C_1$–$C_6$-alkoxy, halogen or nitro, $R^2$ is hydrogen, halogen or amino, $R^3$ is hydrogen and $R^5$–$R^8$ are hydrogen atoms, or $R^6$ and $R^8$ are hydrogen and $R^5$ and $R^7$ together form a bond.

3. Nucleoside of claim 1, wherein Ba is group (A), $R^1$ is amino or nitro and $R^2$, $R^3$, and $R^5$–$R^8$ are each hydrogen or $R^2$, $R^3$, $R^6$ and $R^8$ are hydrogen and $R^5$ and $R^7$ together form a bond.

4. Nucleoside of claim 1, wherein Ba is group (B) and $R^1$, $R^2$ and $R^5$–$R^8$ are each hydrogen.

5. Nucleoside of claim 1, wherein Ba is group (C), $R^1$ is hydrogen, amino or nitro, and $R^2$, $R^3$, $R^5$–$R^8$ each are hydrogen, or $R^2$, $R^3$, $R^6$ and $R^8$ are hydrogen and $R^5$ and $R^7$ together form a bond.

6. Nucleoside of claim 1, wherein Ba is group (D) and $R^1$ is amino or chlorine, and $R^2$ and $R^5$–$R^8$ each are hydrogen.

7. Nucleoside of claim 1, wherein Ba is group (E), $R^1$ is amino or $C_1$–$C_6$-alkoxy and $R^2$ and $R^5$–$R^8$ each are hydrogen.

8. Nucleoside of claim 1, wherein Ba is group (F), $R^2$ is hydrogen or amino and $R^3$ and $R^5$–$R^8$ are each hydrogen.

9. Nucleoside of claim 1, wherein Ba is group (G), $R^2$ is hydrogen, amino or chlorine and $R^3$ and $R^5$–$R^8$ are each hydrogen.

10. Nucleotide of claim 1, wherein said nucleotide is 1-(2,3-didesoxy-$\beta$-D-glyceropentofuranosyl)-1 H-pyrrolo-[2,3-b]pyridine $5^1$-triphosphate or 1-(2,3-didesoxy-$\beta$-D-glyceropent-2-enofuranosyl)-4-nitro-1H-pyrrolo[2,3-b]pyridine $5^1$-triphosphate.

11. Nucleotide of claim 10, wherein said nucleotide is in the form of the triethylammonium salt.

12. Nucleoside derivative of formula I

wherein

Ba is an indolyl, pyrrolopyridinyl, imidazopyridinyl, imidazotriazinyl or imidazopyrimidinyl group;

$R^1$ is hydrogen, amino, C1–C6-alkoxy, halogen or nitro;

$R^2$ is hydrogen, halogen or amino;

$R^3$ is hydrogen;

$R^5$ is hydrogen;

$R^6$ is hydrogen, halogen, cyano or azido;

$R^7$ is hydrogen; and $R^8$ is hydrogen or $R^5$ and $R^7$ together form a bond;

with the proviso that when Ba is the group (E) and $R^1$ is amino, $R^5$ and $R^7$ cannot together represent a bond, as well as their possible $\alpha$ and $\beta$-anomers, $N^7$-, $N^8$- or $N^9$ regioisomers (purine nomenclature), tautomers and salts, and nucleic acids which contain compounds of the formula I as constructional units.

* * * * *